(12) United States Patent
Bussemaker et al.

(10) Patent No.: US 8,483,970 B2
(45) Date of Patent: Jul. 9, 2013

(54) METHOD FOR IDENTIFYING AQTL REGIONS WHOSE GENOTYPE MODULATES TRANSCRIPTION FACTOR ACTIVITY

(75) Inventors: Harmen J. Bussemaker, New York, NY (US); Eunjee Lee, New York, NY (US)

(73) Assignee: The Trustees of Columbia University in the city of New York, New York, NY (US)

( * ) Notice: Subject to any disclaimer, the term of this patent is extended or adjusted under 35 U.S.C. 154(b) by 509 days.

(21) Appl. No.: 12/569,794

(22) Filed: Sep. 29, 2009

(65) Prior Publication Data

US 2010/0153018 A1 Jun. 17, 2010

Related U.S. Application Data

(60) Provisional application No. 61/101,076, filed on Sep. 29, 2008, provisional application No. 61/186,479, filed on Jun. 12, 2009.

(51) Int. Cl.
*G06F 19/00* (2011.01)
*C12Q 1/68* (2006.01)

(52) U.S. Cl.
USPC ............................................ 702/20; 435/6.1

(58) Field of Classification Search
None
See application file for complete search history.

(56) References Cited

U.S. PATENT DOCUMENTS

| 8,219,323 B2 | 7/2012 | Bussemaker et al. |
| 2008/0102460 A1 | 5/2008 | Bussemaker et al. |

OTHER PUBLICATIONS

Han et al., "Comparing Quantitative Trait Loci and Gene Expression Data Associated With a Complex Trait", 2003, Bioinformatics, vol. 1, No. 1, 8 pages.*
Gibson et al. The quantitative genetics of transcription Trends in Genetics vol. 21, pp. 616-623 (2005).*
U.S. Appl. No. 11/803,777, Oct. 14, 2011 Final Office Action.
U.S. Appl. No. 11/803,777, Jun. 17, 2011 Response to Non-Final Office Action.
U.S. Appl. No. 11/803,777, Feb. 17, 2011 Non-Final Office Action.
Zhu J, et al. (2008) "Integrating large-scale functional genomic data to dissect the complexity of yeast regulatory networks." Nat Genet. 40(7): 854-61.
Lee SI, et al. (2006) "Identifying regulatory mechanisms using individual variation reveals key role for chromatin modification." PNAS. 103(38): 14062-7.
Yvert G., et al. (2003) Trans-acting regulatory variation in *Saccharomyces cerevisiae* and the role of transcription factors. Nat Genet. 35(1):57-64.
Kim CG, et al. (2007) "Tamoxifen-induced activation of p21Wafl/Cip1 gene transcription is mediated by Early Growth Response-1 protein through the JNK and p38 MAP kinase/ELK-1 cascades in MDA-MB-361 breast carcinoma cells." Cell Signal. 19(6) : 1290-300.
Stormo, et al., "Quantitative analysis of the relationship between nucleotide sequence and functional activity." Nucleic Acids Res. Aug. 26, 1986;14(16):6661-79.
Schneider, et al., "Sequence logos: a new way to display consensus sequences." Nucleic Acids Res. Oct. 25, 1990;18(20):6097-100.
Bussemaker, et al., "Regulatory element detection using correlation with expression." Nat Genet. Feb. 2001;27(2):167-71.
Liu, et al., "Rationalization of gene regulation by a eukaryotic transcription factor: calculation of regulatory region occupancy from predicted binding affinities." J Mol Biol. Oct. 11, 2002;323(1):1-8.
Roven, et al., "REDUCE: An online tool for inferring cis-regulatory elements and transcriptional module activities from microarray data." Nucleic Acids Res. Jul. 1, 2003;31(13):3487-90.
Djordjevic, et al., "A biophysical approach to transcription factor binding site discovery." Genome Res. Nov. 2003;13(11):2381-90.
Granek, et al., "Explicit equilibrium modeling of transcription-factor binding and gene regulation." Genome Biol. 2005;6(10):R87. Epub Sep. 30, 2005.
Foat, et al., "Profiling condition-specific, genome-wide regulation of mRNA stability in yeast." Proc Natl Acad Sci U S A. Dec. 6, 2005;102(49):17675-80. Epub Nov. 29, 2005.
Tanay, A., "Extensive low-affinity transcriptional interactions in the yeast genome." Genome Res. Aug. 2006;16(8):962-72. Epub Jun. 29, 2006.
Foat, et al., "Statistical mechanical modeling of genome-wide transcription factor occupancy data by MatrixREDUCE." Bioinformatics. Jul. 15, 2006;22(14):e141-9.
U.S. Appl. No. 11/803,777, Jun. 6, 2012 Issue Fee payment.

* cited by examiner

Primary Examiner — John S Brusca
(74) Attorney, Agent, or Firm — Baker Botts, L.L.P.

(57) ABSTRACT

The disclosed subject matter is directed to genetic linkage methods for identifying genetic determinants of transcription factor activity. An inferred transcription factor activity profile is generated based on a nucleotide sequence-specific mathematical model of gene expression regulation. Genetic linkage analysis is performed to identify at least one genetic determinant linked to a specific transcription factor segregant based on the inferred transcription factor profile.

22 Claims, 23 Drawing Sheets

| | | |
|---|---|---|
| ADR1 | GAT1 | LEU3 |
| SUT1 | GLN3 | ARO80 |
| SKN7 | DAL80 | DAL82 |
| SWI5 | DAL81 | MATA1 |
| AGE2 | PUT3 | GAT3 |
| OPI1 | ECM22 | YER051W |
| PHD1 | RPH1 | NRG1 |
| SOK2 | HAC1 | RIM101 |
| MOT3 | HSF1 | SKO1 |
| AFT2 | AZF1 | MAC1 |
| RCS1 | RFX1 | NDD1 |
| MSN4 | SNT2 | YOX1 |
| MSN2 | STP4 | CIN5 |
| STP1 | IXR1 | YAP6 |
| HAP1 | SMP1 | YAP5 |
| MET31 | CHA4 | GTS1 |
| CRZ1 | YDR520C | TEC1 |
| ROX1 | ZAP1 | CST6 |
| STB5 | RLR1 | SPT23 |
| MIG1 | STB4 | RME1 |
| GCR2 | SIP4 | STE12 |
| GCR1 | SUM1 | DIG1 |
| HAP5 | XBP1 | PHO2 |
| HAP2 | SFL1 | ARR1 |
| HAP4 | RLM1 | SPT2 |
| TYE7 | THI2 | YHP1 |
| CBF1 | SNF1 | FKH1 |
| PHO4 | PDR1 | FKH2 |
| MET4 | RDS1 | INO2 |
| MET32 | PDR3 | INO4 |
| MET28 | AGT1 | STB2 |
| YAP7 | YML081W | REB1 |
| CAD1 | ASH1 | YDR026C |
| YAP1 | MCM1 | YRR1 |
| YAP3 | IME1 | SWI6 |
| RTG3 | UME6 | MBP1 |
| GCN4 | RPN4 | SWI4 |
| ARG81 | ABF1 | STB1 |
| BAS1 | GAL80 | SFP1 |
| ARG80 | GAL4 | FHL1 |
| CZF3 | UGA3 | RAP1 |

FIG.2A1   FIG.2A2   FIG.2A3

| TF[a] | # Genes[b] | | | # aQTL[c] | | | # markers[d] | | | Interval(kb)[e] | | |
|---|---|---|---|---|---|---|---|---|---|---|---|---|
| | CIM | t-test | WMW | CIM | t-test | WMW | CIM | t-test | WMW | CIM | t-test | WMW |
| ABF1 | – | 9 | 41 | – | 1 | 2 | – | 3 | 23 | – | 13.61 | 30.49 |
| ACE2 | 16 | 172 | 193 | 1 | 6 | 7 | 4 | 74 | 87 | 26.98 | 46.96 | 46.94 |
| ADR1 | 29 | 142 | 130 | 2 | 8 | 8 | 9 | 69 | 62 | 26.79 | 30.15 | 28.41 |
| AFT2 | 57 | 106 | 99 | 1 | 1 | 1 | 4 | 36 | 35 | 96.12 | 173.69 | 163.81 |
| ARG81 | – | 133 | 146 | – | 2 | 2 | – | 36 | 37 | – | 112.45 | 121.14 |
| ARO80 | 11 | 125 | 130 | 1 | 9 | 10 | 6 | 48 | 47 | 18.43 | 23.06 | 19.73 |
| ARR1 | 18 | 99 | 97 | 1 | 7 | 4 | 5 | 35 | 39 | 28.45 | 25.85 | 45.24 |
| ASH1 | – | 136 | 140 | – | 3 | 3 | – | 10 | 11 | – | 77.23 | 78.84 |
| AZF1 | – | 8 | 19 | – | 1 | 3 | – | 1 | 3 | – | 13.53 | 12.72 |
| BAS1 | – | 4 | 36 | – | 1 | 2 | – | 2 | 18 | – | 8.83 | 29.62 |
| CAD1 | – | 30 | 47 | – | 5 | 9 | – | 15 | 17 | – | 12.25 | 10.76 |
| CBF1 | 21 | 155 | 155 | 1 | 5 | 2 | 11 | 73 | 70 | 33.95 | 49.7 | 124.16 |
| CHA4 | 18 | 127 | 127 | 1 | 8 | 9 | 8 | 50 | 58 | 29.14 | 23.84 | 22.08 |
| CIN5 | 19 | 71 | 71 | 1 | 2 | 2 | 8 | 39 | 39 | 39.6 | 62.82 | 62.82 |
| CRZ1 | – | 20 | 10 | – | 1 | 1 | – | 8 | 7 | – | 31.61 | 18.44 |
| DAL80 | 19 | 19 | 29 | 1 | 1 | 2 | 8 | 8 | 10 | 39.6 | 39.6 | 26.86 |
| DAL81 | – | 36 | 64 | – | 3 | 5 | – | 13 | 23 | – | 24.29 | 24.37 |
| DAL82 | 3 | 100 | 119 | 1 | 15 | 13 | 2 | 109 | 130 | 7.37 | 11.98 | 16.41 |
| DIG1 | 23 | 60 | 60 | 1 | 1 | 1 | 8 | 30 | 30 | 33.26 | 103.33 | 103.33 |
| ECM22 | 35 | 140 | 133 | 2 | 5 | 6 | 13 | 71 | 65 | 35.06 | 47.79 | 37.71 |
| FKH1 | 21 | 248 | 254 | 1 | 6 | 4 | 11 | 104 | 106 | 33.95 | 70.36 | 109.11 |
| FKH2 | 40 | 123 | 206 | 2 | 9 | 11 | 19 | 57 | 74 | 36.78 | 21.3 | 28.9 |
| GAL4 | – | 78 | 91 | – | 2 | 3 | – | 2 | 31 | – | 63.53 | 52.6 |
| GAL80 | 32 | 105 | 147 | 1 | 2 | 2 | 2 | 33 | 35 | 71.43 | 96.5 | 136.85 |
| GAT1 | – | 127 | 128 | – | 13 | 13 | – | 42 | 38 | – | 16.35 | 16.8 |
| GAT3 | 32 | 84 | 91 | 1 | 2 | 2 | 4 | 11 | 23 | 50.27 | 67.88 | 75.46 |
| GCN4 | 26 | 92 | 148 | 1 | 1 | 5 | 26 | 34 | 45 | 45.78 | 155.49 | 49.46 |
| GCR1 | 23 | 129 | 156 | 2 | 13 | 12 | 10 | 42 | 69 | 19.33 | 16.02 | 21.35 |
| GCR2 | 61 | 100 | 110 | 2 | 4 | 6 | 12 | 38 | 40 | 51.27 | 42.93 | 31.86 |
| GLN3 | – | 18 | 72 | – | 2 | 4 | – | 3 | 17 | – | 12.97 | 32.14 |
| GTS1 | – | 23 | 68 | – | 1 | 5 | – | 11 | 16 | – | 40.99 | 23.66 |
| HAC1 | 10 | 141 | 155 | 1 | 4 | 3 | 9 | 60 | 70 | 15.61 | 56.77 | 83.98 |
| HAP1 | 16 | 149 | 149 | 1 | 2 | 2 | 5 | 65 | 65 | 30.51 | 131.43 | 131.43 |
| HAP2 | 15 | 59 | 61 | 1 | 2 | 2 | 7 | 26 | 27 | 25.09 | 46.97 | 47.86 |
| HAP4 | 31 | 71 | 75 | 2 | 6 | 7 | 11 | 27 | 30 | 27.72 | 21.84 | 19.28 |
| HAP5 | 11 | 86 | 86 | 1 | 1 | 1 | 23 | 32 | 32 | 24.08 | 146.73 | 146.73 |
| IME1 | – | 29 | 27 | – | 5 | 5 | – | 16 | 15 | – | 7.9 | 7.65 |
| INO2 | 32 | 153 | 155 | 1 | 2 | 4 | 4 | 38 | 34 | 50.27 | 127.21 | 63.6 |
| INO4 | 32 | 146 | 158 | 1 | 2 | 3 | 4 | 37 | 39 | 50.27 | 121.14 | 86.82 |
| IXR1 | 48 | 116 | 116 | 1 | 1 | 1 | 2 | 12 | 12 | 78.48 | 201.24 | 201.24 |
| LEU3 | 38 | 146 | 134 | 2 | 7 | 4 | 33 | 53 | 49 | 36.09 | 35.24 | 56.9 |

FIG.4A

| | | | | | | | | | | | | |
|---|---|---|---|---|---|---|---|---|---|---|---|---|
| MAC1 | – | 0 | – | – | 1 | – | – | 1 | – | – | 0.2 | – |
| MATA1 | 19 | 81 | 64 | 1 | 2 | 1 | 3 | 8 | 7 | 32.9 | 73.5 | 105.7 |
| MBP1 | – | 105 | 106 | – | 8 | 9 | – | 40 | 39 | – | 21.78 | 19.36 |
| MCM1 | 32 | 113 | 114 | 1 | 1 | 2 | 4 | 37 | 35 | 50.27 | 185.83 | 92.91 |
| MET28 | 32 | 90 | 90 | 1 | 1 | 1 | 4 | 32 | 32 | 50.27 | 149.03 | 149.03 |
| MET31 | 19 | 74 | 74 | 1 | 2 | 2 | 8 | 42 | 42 | 39.6 | 65.43 | 65.43 |
| MET32 | 19 | 86 | 97 | 1 | 4 | 5 | 8 | 53 | 66 | 39.6 | 38.94 | 34.55 |
| MET4 | 16 | 74 | 75 | 1 | 1 | 2 | 5 | 40 | 40 | 29.31 | 134.18 | 65.45 |
| MIG1 | 26 | 26 | – | 1 | 1 | – | 1 | 1 | – | 34.55 | 34.55 | – |
| MOT3 | 57 | 118 | 118 | 1 | 2 | 2 | 4 | 10 | 10 | 96.12 | 98.01 | 98.01 |
| MSN2 | 19 | 73 | 78 | 1 | 7 | 4 | 8 | 33 | 38 | 39.6 | 18.24 | 33.67 |
| MSN4 | 11 | 19 | 19 | 1 | 1 | 1 | 2 | 8 | 8 | 21.28 | 39.6 | 39.6 |
| NDD1 | – | 46 | 63 | – | 1 | 1 | – | 3 | 6 | – | 72.81 | 104.89 |
| NRG1 | 11 | 38 | 4 | 1 | 5 | 1 | 2 | 7 | 1 | 21.28 | 14.12 | 5.83 |
| OPI1 | – | 1 | 6 | – | 1 | 2 | – | 1 | 2 | – | 0.15 | 4.38 |
| PDR1 | – | 124 | 122 | – | 9 | 5 | – | 37 | 43 | – | 23.96 | 43.12 |
| PDR3 | – | 99 | 199 | – | 2 | 9 | – | 15 | 32 | – | 91.06 | 37.64 |
| PHD1 | 34 | 73 | 106 | 1 | 7 | 9 | 1 | 10 | 21 | 62.19 | 17.09 | 17.75 |
| PHO2 | 18 | 111 | 107 | 1 | 2 | 3 | 9 | 54 | 51 | 34.36 | 92.24 | 59.73 |
| PUT3 | – | 9 | 8 | – | 3 | 1 | – | 7 | 2 | – | 5.16 | 11.68 |
| RAP1 | 32 | 99 | 106 | 1 | 1 | 1 | 4 | 35 | 36 | 50.27 | 163.81 | 173.69 |
| RCS1 | – | 6 | 41 | – | 1 | 3 | – | 2 | 6 | – | 8.17 | 24.04 |
| RDS1 | 17 | 101 | 133 | 1 | 3 | 7 | 7 | 10 | 22 | 23.45 | 52.41 | 28.64 |
| REB1 | – | 59 | 78 | – | 6 | 4 | – | 20 | 26 | – | 14.54 | 32.67 |
| RFX1 | 49 | 112 | 112 | 2 | 3 | 3 | 11 | 60 | 60 | 42.32 | 60.16 | 60.16 |
| RGT1 | – | 51 | 50 | – | 4 | 3 | – | 13 | 14 | – | 20.73 | 27.63 |
| RIM101 | 37 | 106 | 110 | 2 | 1 | 2 | 31 | 36 | 37 | 31.64 | 173.69 | 90.05 |
| RLM1 | – | 56 | 110 | – | 7 | 7 | – | 26 | 44 | – | 14.82 | 28.53 |
| RLR1 | 13 | 62 | 62 | 1 | 3 | 4 | 18 | 111 | 110 | 30.39 | 38.89 | 29.17 |
| RME1 | 16 | 95 | 88 | 1 | 4 | 4 | 7 | 39 | 40 | 20 | 36.02 | 35.23 |
| ROX1 | – | 34 | 48 | – | 1 | 1 | – | 1 | 2 | – | 62.19 | 87.34 |
| RPH1 | – | 19 | 28 | – | 1 | 2 | – | 6 | 8 | – | 34.72 | 27.47 |
| RPN4 | – | – | 50 | – | – | 2 | – | – | 2 | – | – | 40.83 |
| RTG3 | – | 20 | 19 | – | 2 | 3 | – | 13 | 21 | – | 15.2 | 10.97 |
| SFL1 | 53 | 80 | 142 | 2 | 6 | 9 | 12 | 21 | 42 | 51.12 | 23.42 | 27.98 |
| SFP1 | – | 78 | 37 | – | 4 | 3 | – | 10 | 7 | – | 35.06 | 21.54 |
| SIP4 | – | 16 | – | – | 1 | – | – | 1 | – | – | 20.43 | – |
| SKN7 | 30 | 77 | 85 | 2 | 7 | 5 | 9 | 19 | 26 | 29.44 | 20.55 | 33.78 |
| SKO1 | 30 | 184 | 232 | 2 | 5 | 4 | 13 | 78 | 92 | 28.85 | 64.69 | 98.08 |
| SMP1 | 46 | 74 | 76 | 1 | 2 | 2 | 9 | 29 | 31 | 71.33 | 61.07 | 63.15 |
| SNF1 | 11 | 111 | 128 | 1 | 8 | 5 | 1 | 48 | 59 | 15.13 | 21.77 | 41.4 |
| SNT2 | 19 | 102 | 102 | 1 | 5 | 5 | 8 | 18 | 16 | 39.6 | 36.08 | 35.18 |
| SOK2 | – | 33 | 44 | – | 6 | 5 | – | 13 | 19 | – | 9.85 | 16.92 |
| SPT2 | 19 | 115 | 115 | 1 | 2 | 2 | 16 | 43 | 43 | 36.64 | 99.42 | 99.42 |

FIG.4B

| | | | | | | | | | | | |
|---|---|---|---|---|---|---|---|---|---|---|---|
| SPT23 | 4 | 77 | 43 | 1 | 2 | 3 | 1 | 7 | 5 | 5.83 | 69.41 | 24.7 |
| STB1 | 42 | 179 | 265 | 2 | 12 | 16 | 5 | 56 | 89 | 36.23 | 24.39 | 28.49 |
| STB2 | 34 | 34 | 34 | 1 | 1 | 1 | 1 | 1 | 1 | 62.19 | 62.19 | 62.19 |
| STB4 | 19 | 52 | 26 | 1 | 3 | 1 | 25 | 29 | 26 | 35.9 | 28.24 | 45.78 |
| STB5 | 47 | 120 | 120 | 1 | 2 | 2 | 1 | 15 | 15 | 76.75 | 99.84 | 99.84 |
| STE12 | 23 | 73 | 73 | 1 | 1 | 1 | 8 | 32 | 32 | 33.26 | 130.16 | 130.16 |
| STP4 | – | – | 23 | – | – | 4 | – | – | 7 | – | – | 10.49 |
| SUM1 | – | 84 | 63 | – | 3 | 2 | – | 5 | 5 | – | 48.46 | 50.29 |
| SUT1 | 37 | 158 | 139 | 2 | 11 | 8 | 16 | 72 | 75 | 34.37 | 22.37 | 28.61 |
| SWI4 | – | 59 | 59 | – | 5 | 6 | – | 10 | 12 | – | 19.7 | 17.52 |
| SWI5 | 78 | 187 | 184 | 2 | 1 | 2 | 15 | 78 | 78 | 65.04 | 304.4 | 149.39 |
| TEC1 | – | 37 | 19 | – | 5 | 3 | – | 95 | 85 | – | 13.62 | 13.96 |
| THI2 | – | 33 | 29 | – | 5 | 5 | – | 17 | 11 | – | 13.63 | 12.19 |
| TYE7 | – | 31 | 22 | – | 3 | 1 | – | 3 | 1 | – | 15.42 | 34.19 |
| UGA3 | 57 | 136 | 136 | 1 | 2 | 2 | 23 | 39 | 39 | 93.97 | 109.36 | 109.36 |
| UME6 | – | – | 15 | – | – | 1 | – | – | 7 | – | – | 25.09 |
| XBP1 | – | 5 | 13 | – | 1 | 3 | – | 1 | 4 | – | 8.21 | 9.2 |
| YAP1 | – | 22 | 16 | – | 3 | 2 | – | 12 | 10 | – | 13.44 | 17.75 |
| YAP3 | – | 54 | 62 | – | 3 | 4 | – | 23 | 30 | – | 25.26 | 23.71 |
| YAP5 | 42 | 194 | 226 | 2 | 11 | 15 | 6 | 65 | 77 | 33.5 | 28.47 | 24.48 |
| YAP6 | – | – | 27 | – | – | 1 | – | – | 1 | – | – | 45.02 |
| YAP7 | – | 59 | 107 | – | 5 | 11 | – | 19 | 32 | – | 18.19 | 16.59 |
| YDR026C | – | 30 | 30 | – | 4 | 4 | – | 7 | 7 | – | 10.4 | 10.4 |
| YER051W | 11 | 20 | 11 | 1 | 2 | 2 | 2 | 4 | 2 | 21.28 | 19.33 | 10.36 |
| YHP1 | 11 | 17 | 17 | 1 | 1 | 1 | 2 | 6 | 6 | 24.11 | 33.82 | 33.82 |
| YML081W | 19 | 231 | 202 | 1 | 5 | 6 | 10 | 112 | 99 | 33.41 | 80.01 | 57.24 |
| YOX1 | – | 57 | 50 | – | 5 | 4 | – | 30 | 7 | – | 19.03 | 21.99 |
| YRR1 | 48 | 115 | 126 | 2 | 5 | 9 | 9 | 25 | 33 | 40.39 | 36.81 | 21.93 |
| ZAP1 | 9 | 66 | 65 | 1 | 5 | 4 | 4 | 30 | 30 | 18.88 | 24.42 | 30.52 |
| Average | 28 | 83 | 91 | 1.2 | 3.8 | 4.2 | 8.7 | 30.5 | 33.7 | 38.7 | 54.3 | 51.7 |

[a]Transcription factor.
[b]Number of genes in aQTL region(s).
[c]Number of disjoint aQTL regions.
[d]Number of markers associated with TF activity.
[e]Average range of disjoint aQTL regions.

FIG.4C

| eQTL region | Transcription Factor | Causal gene | Interaction type | Zhu et al.[1] prediction | | Lee et al.[2] prediction | | Sun et al.[3] TF implicated | Ye et al.[4] TF implicated |
|---|---|---|---|---|---|---|---|---|---|
| | | | | eQTL hotspot | TF Implicated | Module | TF implicated | | |
| Chr1:55330-89878 | MIG1 | – | – | – | – | #26 | – | – | – |
| Chr2:352258-368059 | GCR1 | – | – | – | – | – | – | – | – |
| Chr2:352258-368990 | YAP5 | – | – | – | – | – | – | – | – |
| Chr2:368992-391855 | GCR1 | – | – | #1 | – | #136 | – | – | – |
| Chr2:427684-499011 | SMP1 | – | – | – | – | #148 | – | – | – |
| Chr2:514036-548400 | PHO2 | – | – | – | – | – | – | – | – |
| Chr2:521416-548400 | ACE2 | – | – | – | – | – | – | 4 | 4 |
| Chr2:533269-548400 | SNF1 | – | – | – | – | – | – | – | – |
| Chr2:533269-562408 | CHA4 | – | – | #2 | – | – | – | – | – |
| Chr2:533269-562408 | SUT1 | – | – | #2 | – | – | – | – | – |
| Chr2:533269-567220 | CBF1 | – | – | #2 | – | #43 | – | – | – |
| Chr2:533269-567220 | FKH1 | CDC28 | PI | #2 | – | #43 | – | – | 4 |
| Chr2:533269-567220 | FKH2 | CDC28 | PI | #2 | – | #43 | – | – | – |
| Chr2:533269-567220 | GCR2 | – | – | #2 | – | #43 | – | – | – |
| Chr2:533269-567220 | SKO1 | – | – | #2 | – | #43 | – | – | – |
| Chr2:533269-567220 | SWI5 | CDC28 | PI | #2 | – | #43 | – | 4 | 4 |
| Chr2:537315-562408 | HAP2 | – | – | #2 | – | – | – | – | – |
| Chr2:537315-551298 | ADR1 | CNS1 | PI | #2 | – | – | – | – | – |
| Chr2:553813-569419 | HAC1 | – | – | #2 | – | #43 | – | – | – |
| Chr2:555788-567220 | STB1 | CDC28 | PI | #2 | – | #43 | – | – | – |
| Chr2:562416-582418 | RME1 | – | – | #2 | – | #43 | – | – | – |
| Chr2:569415-592862 | RDS1 | – | – | #2 | – | #43 | – | – | – |
| Chr3:54437-100212 | GCN4 | – | – | #4 | – | #86 | – | – | 4 |
| Chr3:64312-100212 | LEU3 | – | – | #4 | – | #86 | 4 | – | 4 |
| Chr3:64312-100212 | RIM101 | – | – | #4 | – | #86 | – | – | – |
| Chr3:64312-100212 | STB4 | BIK1 | PI | #4 | – | #86 | – | – | – |
| Chr3:76128-100212 | HAP5 | – | – | #4 | – | #86 | – | – | – |
| Chr3:81833-175798 | UGA3 | – | – | #4 | – | – | – | – | – |
| Chr3:105043-201165 | AFT2 | – | – | #4 | – | – | – | – | – |
| Chr3:105043-201165 | MOT3 | – | – | #4 | – | – | – | – | – |
| Chr3:105043-201165 | SWI5 | – | – | #4 | – | – | – | – | – |
| Chr3:177851-210747 | MATA1 | – | – | #5 | – | – | – | – | – |
| Chr3:177851-228124 | GAT3 | – | – | #5 | – | – | – | – | – |
| Chr3:177851-228124 | INO2 | – | – | #5 | – | – | – | – | – |
| Chr3:177851-228124 | INO4 | – | – | #5 | – | – | – | – | – |
| Chr3:177851-228124 | MCM1 | MATα1, MATα2 | PI | #5 | – | – | – | – | – |
| Chr3:177851-228124 | MET28 | – | – | #5 | – | – | – | – | – |
| Chr3:177851-228124 | RAP1 | – | – | #5 | – | – | – | – | – |

FIG.8A

| Location | Gene | Col3 | Col4 | Col5 | Col6 | Col7 | Col8 | Col9 | Col10 |
|---|---|---|---|---|---|---|---|---|---|
| Chr3:177851-228124 | YAP5 | – | – | #5 | – | – | – | – | – |
| Chr3:177851-228124 | YRR1 | – | – | #5 | – | – | – | – | – |
| Chr4:518401-555042 | SPT2 | – | – | – | – | #67 | – | – | – |
| Chr4:1109730-1181159 | GAL80 | – | – | – | – | – | – | – | – |
| Chr4:1321551-1400032 | IXR1 | – | – | – | – | #128 | – | – | – |
| Chr5:251648-312671 | STB1 | – | – | – | – | – | – | – | – |
| Chr5:333253-395441 | PHD1 | FLO8 | GI | – | – | – | – | 4 | – |
| Chr5:333253-395441 | STB2 | – | – | – | – | – | – | – | – |
| Chr5:395443-458084 | SFL1 | – | – | – | – | – | – | – | – |
| Chr5:420596-426428 | SPT23 | – | – | – | – | – | – | – | – |
| Chr7:375500-402870 | RIM101 | – | – | – | – | #73 | – | – | – |
| Chr8:95470-128731 | DIG1 | – | – | #7 | 4 | – | – | 4 | 4 |
| Chr8:95470-128731 | STE12 | GPA1, STE20 | GI | #7 | 4 | – | – | 4 | – |
| Chr8:441791-518538 | STB5 | STB5 | Local | – | – | – | – | – | – |
| Chr9:19651-27025 | DAL82 | – | – | – | – | – | – | – | – |
| Chr10:204138-227893 | SKO1 | – | – | – | – | – | – | – | – |
| Chr12:508030-553063 | RFX1 | RFX1 | Local | – | – | – | – | – | – |
| Chr12:644137-668248 | YHP1 | – | – | – | – | #76 | – | – | – |
| Chr12:644137-674650 | ECM22 | HAP1 | GI | #8 | – | #76 | – | – | – |
| Chr12:644137-674650 | HAP1 | – | Local | #8 | 4 | #76 | 4 | 4 | 4 |
| Chr12:644137-674650 | YRR1 | – | – | #8 | – | #76 | – | – | – |
| Chr13:27644-46069 | ARO80 | – | – | – | – | #54 | – | – | – |
| Chr13:28695-64969 | LEU3 | – | – | #10 | – | #4 | – | – | – |
| Chr13:46085-64969 | ZAP1 | – | – | #10 | – | #4 | – | – | – |
| Chr14:418270-486860 | GCR2 | – | – | #11 | – | #94 | – | – | – |
| Chr15:17947-48334 | RLR1 | – | – | – | – | #70 | – | – | – |
| Chr15:141634-170944 | MET4 | – | – | #12 | – | #59 | – | – | – |
| Chr15:154310-175593 | HAP4 | – | – | #12 | – | – | – | – | – |
| Chr15:154310-175593 | MSN4 | – | – | #12 | – | – | – | – | – |
| Chr15:154310-175593 | NRG1 | – | – | #12 | – | – | – | – | – |
| Chr15:154310-175593 | YER051W | – | – | #12 | – | – | – | – | – |
| Chr15:154310-193910 | ADR1 | – | – | #12 | – | – | – | – | – |
| Chr15:154310-193910 | CIN5 | – | – | #12 | – | – | – | – | 4 |
| Chr15:154310-193910 | DAL80 | – | – | #12 | – | – | – | – | – |
| Chr15:154310-193910 | ECM22 | – | – | #12 | – | – | – | – | – |
| Chr15:154310-193910 | FKH2 | – | – | #12 | – | – | – | – | 4 |
| Chr15:154310-193910 | MET31 | – | – | #12 | – | – | – | – | – |
| Chr15:154310-193910 | MET32 | – | – | #12 | – | – | – | – | – |
| Chr15:154310-193910 | MSN2 | – | – | #12 | – | – | – | – | – |
| Chr15:154310-193910 | RFX1 | – | – | #12 | – | – | – | – | – |
| Chr15:154310-193910 | SFL1 | – | – | #12 | – | – | – | – | – |
| Chr15:154310-193910 | SKN7 | – | – | #12 | – | – | – | – | 4 |
| Chr15:154310-193910 | SNT2 | – | – | #12 | – | – | – | – | – |
| Chr15:154310-193910 | SUT1 | – | – | #12 | – | – | – | – | – |
| Chr15:428239-461651 | YML081W | – | – | – | – | #160 | – | – | – |
| Chr15:546198-580353 | HAP4 | – | – | #13 | 4 | – | – | – | 4 |
| Chr15:551820-571102 | SKN7 | – | – | – | – | #196 | – | – | – |
| Chr16:408884-437334 | ARR1 | – | – | – | – | – | – | – | – |

FIG.8B

| TF | aQTL Region | Maximum LOD Score | Causal Gene[a] | Interaction Type[b] | Polymorphism of Causal Gene |
|---|---|---|---|---|---|
| Hap1p | Chr12:644,137–674,650 | 29.42 | HAP1 | – | BY strains have a Ty1 insertion in the C-terminus |
| Rfx1p | Chr12:508,030–553,063 | 4.83 | RFX1 | – | Transcript of RM strains contains in-frame stops |
| Stb5p | Chr8:441,791–518,538 | 11.47 | STB5 | – | 5 mutations: V142A, Y340H, S579Y, E580D, I581L |
| Adr1p | Chr2:537,315–551,298 | 4.59 | CNS1 | PI | 1 mutation: P187Q<br>One point mutation in 5′UTR |
| Ecm22p | Chr12:644,137–674,650 | 13.14 | HAP1 | GI | By strains have a Ty1 insertion in the C-terminus<br>No AA change |
| Fkh1p | Chr2:533,269–567,220 | 20.28 | CDC28 | PI | One point mutation in 3′UTR/One point mutation in 5′UTR<br>No AA change |
| Fkh2p | Chr2:533,269–567,220 | 10.76 | CDC28 | PI | One point mutation in 3′UTR/One point mutation in 5′UTR<br>No AA change |
| Stb1p | Chr2:555,788–567,220 | 4.86 | CDC28 | PI | One point mutation in 3′UTR/One point mutation in 5′UTR<br>No AA change |
| Swi5p | Chr2:533,269–567,220 | 31.14 | CDC28 | PI | One point mutation in 3′UTR/One point mutation in 5′UTR |
| Mcm1p | Chr3:177,851–228,124 | 38.18 | MATα1 | PI | Only BY strains can express MATα1 gene |
| Mcm1p | Chr3:177,851–228,124 | 38.18 | MATα2 | PI | Only BY strains can express MATα2 gene |
| Phd1p | Chr5:333,253–395,441 | 4.92 | FLO8 | GI | BY strains have a mutation in this gene |
| Stb4p | Chr3:64,312–100,212 | 7.22 | BIK1* | PI | No AA change |
| Ste12p | Chr8:95,470–128,731 | 17.57 | STE20 | GI | Two point mutation: I469S, A194V |
| Ste12p | Chr8:98,514–128,731 | 17.57 | GPA1 | GI | Seven point mutation: A28T, D34N, T47I, I134M, A485T, S551Y, N839D |

[a]Gene in aQTL regions interacting with TF.
[b]Types of Interaction, PI represents physical interaction, and GI represents genetic interaction.
*A questionable modulator. LEU2 within this aQTL region is more plausible modulator of Stb4p.

FIG.9

| TF | SGD description | Causal gene | SGD description | E[DI]a | p-valueb |
|---|---|---|---|---|---|
| Hap1 | Zinc finger transcription factor involved in the complex regulation of gene expression in response to levels of heme and oxygen | HAP1 | | | |
| Rfx1 | Major transcriptional repressor of DNA-damage-regulated genes, recruits repressors Tup1p and Cyc8p to their promoters | RFX1 | | | |
| Stb5 | Activator of multidrug resistance genes, forms a heterodimer with Pdr1p | STB5 | | | |
| Adr1 | Carbon source-responsive zinc-finger transcription factor, required for transcription of the glucose-repressed gene ADH2 | CNS1 | TPR-containing co-chaperone; binds both Hsp82p (Hsp90) and Ssa1p (Hsp70) | 0.046 | $9.2 \times 10^{-4}$ |
| Ecm22 | Sterol regulatory element binding protein, regulates transcription of sterol biosynthetic genes | HAP1 | Zinc finger transcription factor involved in the complex regulation of gene expression in response to levels of heme and oxygen | 0.024 | $2.4 \times 10^{-4}$ |
| Fkh1 | Forkhead family transcription factor with a minor role in the expression of G2/M phase genes | CDC28 | Catalytic subunit of the main cell cycle cyclin-dependent kinase | 0.133 | $7.6 \times 10^{-3}$ |
| Fkh2 | Forkhead family transcription factor with a major role in the expression of G2/M phase genes | CDC28 | Catalytic subunit of the main cell cycle cyclin-dependent kinase | 0.105 | $4.8 \times 10^{-3}$ |
| STB1 | Protein with a role in regulation of MBF-specific transcription at Start, phosphorylated by Cln-Cdc28p kinases in vitro | CDC28 | Catalytic subunit of the main cell cycle cyclin-dependent kinase | 0.007 | $1.7 \times 10^{-5}$ |
| Swi5 | Transcription factor that activates transcription of genes expressed at the M/G1 phase boundary and in G1 phase | CDC28 | Catalytic subunit of the main cell cycle cyclin-dependent kinase | 0.255 | $2.6 \times 10^{-2}$ |
| Mcm1 | Transcription factor involved in cell-type-specific transcription and pheromone response | MATα1 | Transcriptional co-activator involved in regulation of mating-type-specific gene expression | 0.117 | $2.0 \times 10^{-4}$ |
| Mcm1 | Transcription factor involved in cell-type-specific transcription and pheromone response | MATα2 | Homeobox-domain protein that, with Mcm1p, represses a-specific genes in haploids | 0.117 | $2.0 \times 10^{-4}$ |
| Phd1 | Transcriptional activator that enhances pseudohyphal growth | FLO8 | Transcription factor required for flocculation, diploid filamentous growth, and haploid invasive growth | 0.085 | $3.1 \times 10^{-3}$ |

FIG.14A

| | | | | | |
|---|---|---|---|---|---|
| Stb4 | Protein that binds Sin3p in a two-hybrid assay; contains a Zn(II)2Cys6 zinc finger domain characteristic of DNA-binding proteins | BIK1 | Microtubule-associated protein, component of the interface between microtubules and kinetochore, involved in sister chromatid separation | 0.015 | $9.4 \times 10^{-5}$ |
| Ste12 | Transcription factor that is activated by a MAP kinase signaling cascade, activates genes involved in mating or pseudohyphal/invasive growth pathways | GPA1 | GTP-binding alpha subunit of the heterotrimeric G protein that couples to pheromone receptors | 0.287 | $2.8 \times 10^{-3}$ |
| Ste12 | Transcription factor that is activated by a MAP kinase signaling cascade, activates genes involved in mating or pseudohyphal/invasive growth pathways | STE20 | Signal transducing kinase of the PAK (p21-activated kinase) family, involved in pheromone response and pseudohyphal/invasive growth pathways, activated by Cdc42p | 0.287 | $2.8 \times 10^{-3}$ |

$^a$Expected number of genes in each aQTL region interacting with TF.
$^b$p-value quantifying the statistical significance of the identified direct interaction; see Methods.

FIG. 14B

METHOD FOR IDENTIFYING AQTL REGIONS WHOSE GENOTYPE MODULATES TRANSCRIPTION FACTOR ACTIVITY

CROSS REFERENCE TO RELATED APPLICATIONS

This application claims priority to U.S. Provisional Application Ser. No. 61/101,076, filed Sep. 29, 2008, and U.S. Provisional Application Ser. No. 61/186,479, filed Jun. 12, 2009, which are incorporated herein by reference in their entireties.

STATEMENT REGARDING FEDERALLY SPONSORED RESEARCH OR DEVELOPMENT

This invention was made with government support under Grant Nos. HG003008 and U54CA121852, awarded by the National Institute of Health. The government has certain rights in the invention.

BACKGROUND

Predicting phenotype from genotype, in terms of the various molecular processes that govern the behavior of the cell, is one of the central goals of biology. Gene expression levels are an intermediate molecular phenotype of great utility. In recent years, parallel high-throughput genotyping and mRNA expression profiling have enabled researchers to start asking quantitative questions regarding the genetics of gene expression in a variety of organisms, and have revealed that steady-state mRNA abundance is highly heritable for the majority of genes.

Genetic mapping has been applied to high-throughput expression data to identify expression quantitative trait loci (eQTLs) that influence the expression level of individual genes. While sequence polymorphisms in cis-regulatory regions account for part of the genetic variation in expression, some is due to trans-acting polymorphisms at distal loci. The influences of such loci on the transcription factor rate and/or mRNA half-life of individual genes can be quite indirect, but nucleotide-binding, trans-acting factors play a mediating role.

There remains a need in the art to account for the existence of gene regulatory networks that allow for more sensitive detection of cis- and trans-acting polymorphisms. Although approaches that identify subsets of co-expressed genes have been used, they are generally most useful when only a relatively small number of cell state parameters are perturbed, and the expression of large subsets of genes changes in a coherent way. Such methods can be less naturally suitable for analyzing natural genetic variation in gene expression, where the segregation of alleles in the cross causes a large number of cell state parameters to be independently perturbed.

Approaches based on the linear decomposition of the matrix of genes by segregants have also been explored, such as Principal Component Analysis (PCA), which exploits the correlation structure of the gene expression matrix, or Network Component Analysis, which extends PCA by incorporating qualitative information about regulatory network topology. While these methods increase statistical power compared to a single gene based approaches, there remains a need in the art to more fully account for the heritable variation in gene expression.

SUMMARY

The disclosed subject matter provides techniques for identifying one or more genetic determinants of transcription factor activity. In an exemplary embodiment, one method includes generating an inferred transcription factor activity profile based on a nucleotide sequence-specific mathematical model of gene expression regulation and performing genetic analysis to identify at least one genetic determinant linked to a specific transcription factor segregant based on said inferred transcription factor profile.

In another exemplary embodiment, the disclosed subject matter describes a method for identifying aQTL regions whose genotype modulates transcription factor activity. The method can include generating a promoter affinity profile based on a genomic sequence and a position-specific affinity matrix, generating an inferred transcription factor activity profile based on the promoter affinity profile and a gene expression data set, and identifying an aQTL region for a transcription factor based on the transcription factor activity profile and a genotype data set.

The accompanying drawings, which are incorporated and constitute part of this disclosure, illustrate the various exemplary embodiments of the present disclosed subject matter and serve to explain its principles.

BRIEF DESCRIPTION OF THE DRAWINGS

FIG. 2A (including FIGS. 2A1, 2A2, and 2A3) shows a correlation matrix for all pairs of TF binding activity. FIG. 2B shows pairs of TFs whose promoter affinity profiles are correlated across genes (correlation >0.5), as well as their significant aQTL regions.

FIG. 3A shows the estimated FDR using the CIM test, FIG. 3B shows the estimated FDR using the Wilcoxon-Mann-Whitney test, and FIG. 3C shows the estimated FDR using Welch's t-test.

FIG. 4 lists results of genetic linkage analysis using various tests.

FIG. 8 lists the aQTLs identified by an exemplary embodiment of the disclosed subject matter and a comparison of the results using the disclosed method and the methods disclosed in certain prior art.

FIG. 9 lists the transcription factors for which a causal gene was identified.

FIG. 12A shows that Leu3p, Stb4p, and Gcn4p are modulated by a locus on chromosome III that contains the LEU2 gene. FIG. 12B shows that Swi5p, Fkh1p, Fkh2p, and Stb1p map to regions on chromosome II that contains the CDC28 gene. FIG. 12C shows that the aQTL regions for Ste12p contains the STE20 and GPA1 genes. FIG.

12D shows that Mcm1p activity maps to an aQTL containing the MATα1 and MATα2 genes on chromosome III, which only the BY strain expresses.

Figure 13A:
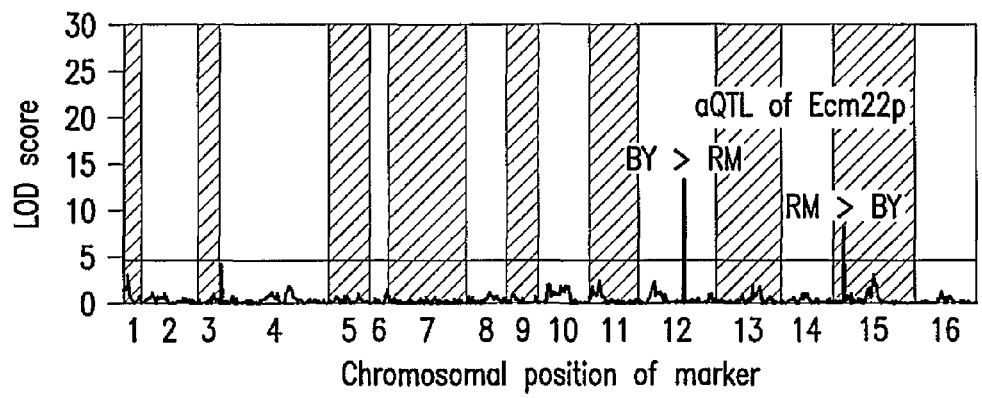
Figure 13B:
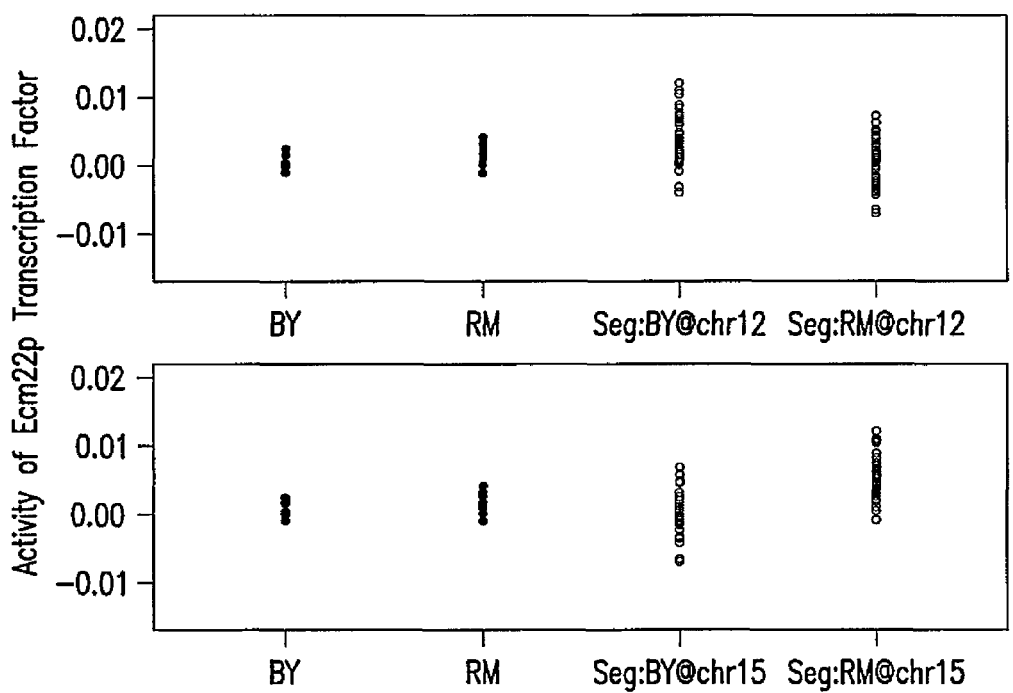
Figure 13C:
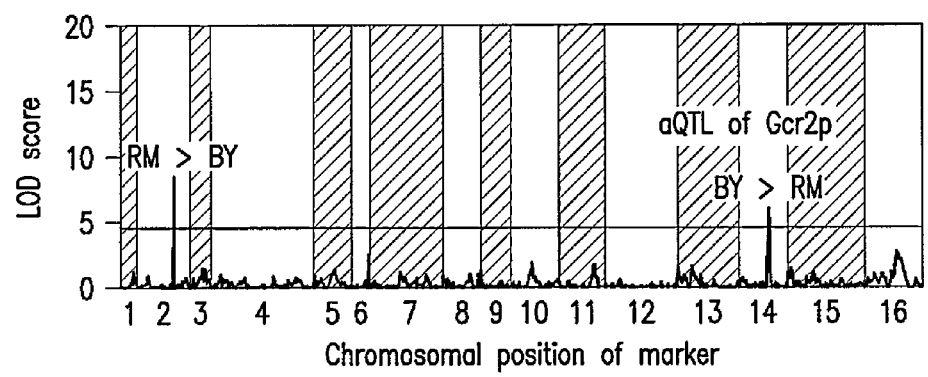
Figure 13D:
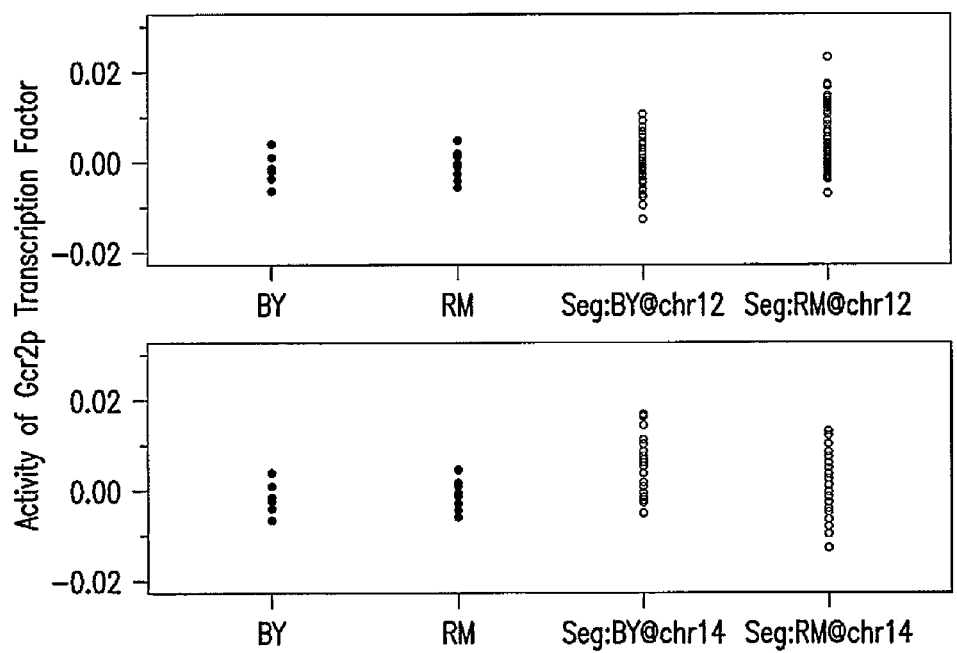

FIG. 13A-13C illustrate the transgressive segregation of Ecm22 and Gcn2 activity. FIG. 13A illustrates the aQTL profiling of ECM22, while FIG. 13C illustrates the inferred activity of transcription factor Ecn22 in parental strains and segregants. FIGS. 13C and 13D illustrate the same information for Gcn2.

FIG. 14 lists transcription factors and their modulators identified in a second exemplary embodiment of the disclosed subject matter.

Figure 15A:
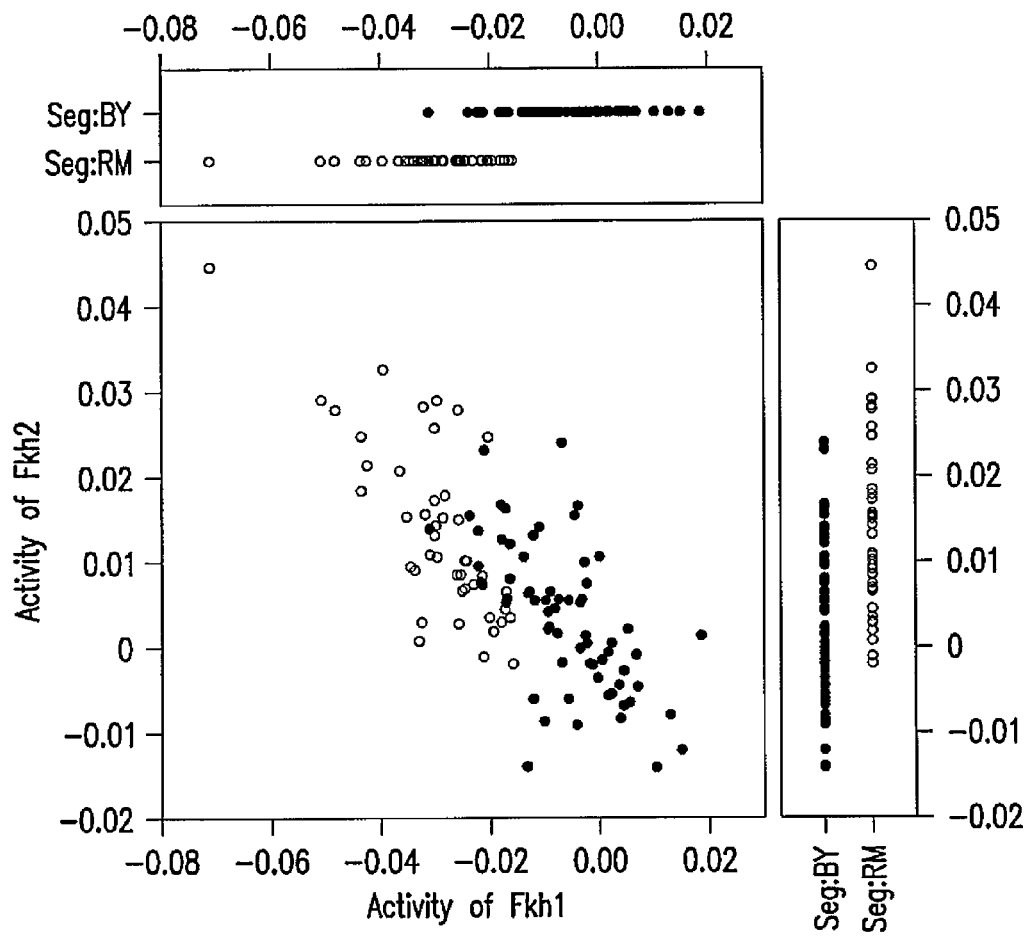
Figure 15B:
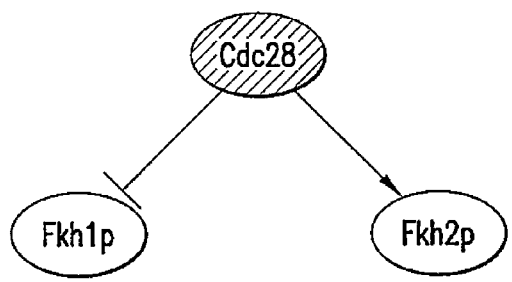

FIG. 15A shows the activity of Fkh1p and Fkh2p across all segregants. FIG. 15B illustrates the antagonistic modulation of Fkh1p and Fkh2p by Cdc28p.

SEQUENCE LISTING

The specification further incorporates by reference the Sequence Listing submitted herewith via EFS on Feb. 22, 2010. Pursuant to 37 C.F.R. §1.52(e)(5), the Sequence Listing text file, identified as 0700503865seglist.txt, is 785 bytes and was created on Feb. 19, 2010. The Sequence Listing, electronically filed herewith, does not extend beyond the scope of the specification and thus does not contain new matter.

DETAILED DESCRIPTION

The presently disclosed subject matter provides techniques for identifying the genetic determinants of transcription factor activity by treating transcription factor activity as a quantitative trait. A transcription factor activity profile is generated based on a nucleotide sequence-specific mathematical model of gene expression regulation. The transcription factor activity can be inferred from quantitative prior information about the DNA binding specificity of transcription factors and gene expression data. Then, genetic linkage analysis can be performed to identify a genetic determinant, such as an activity quantitative trait loci region, linked to a specific transcription factor. The genetic linkage analysis can be based on the inferred transcription factor activity.

Figure 1A:
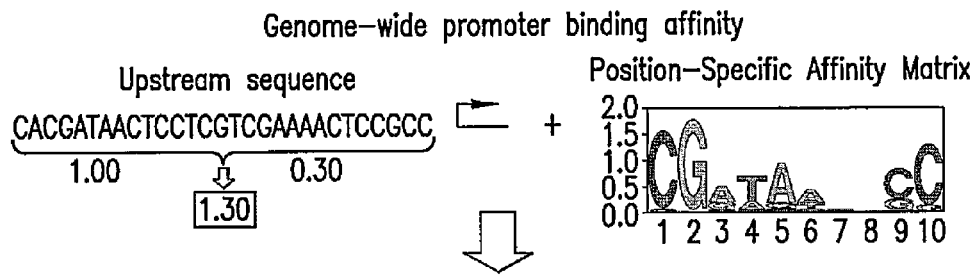
FIGS. 1A-1C illustrate an exemplary embodiment of a process for identifying aQTL regions for transcription factors.
Figure 1B:
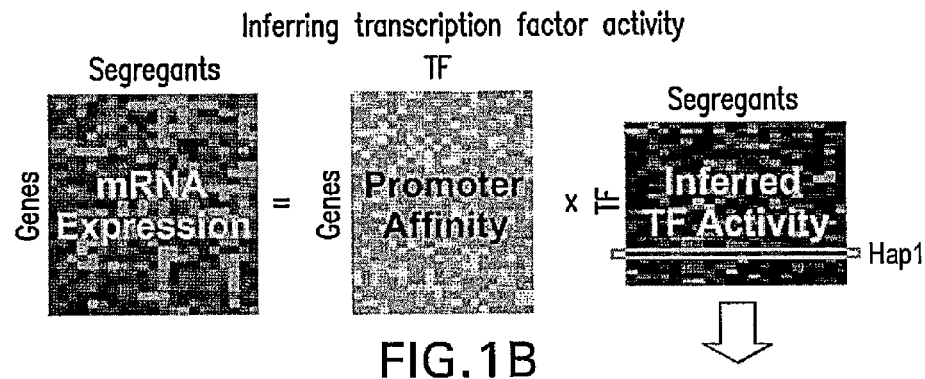
Figure 1C:
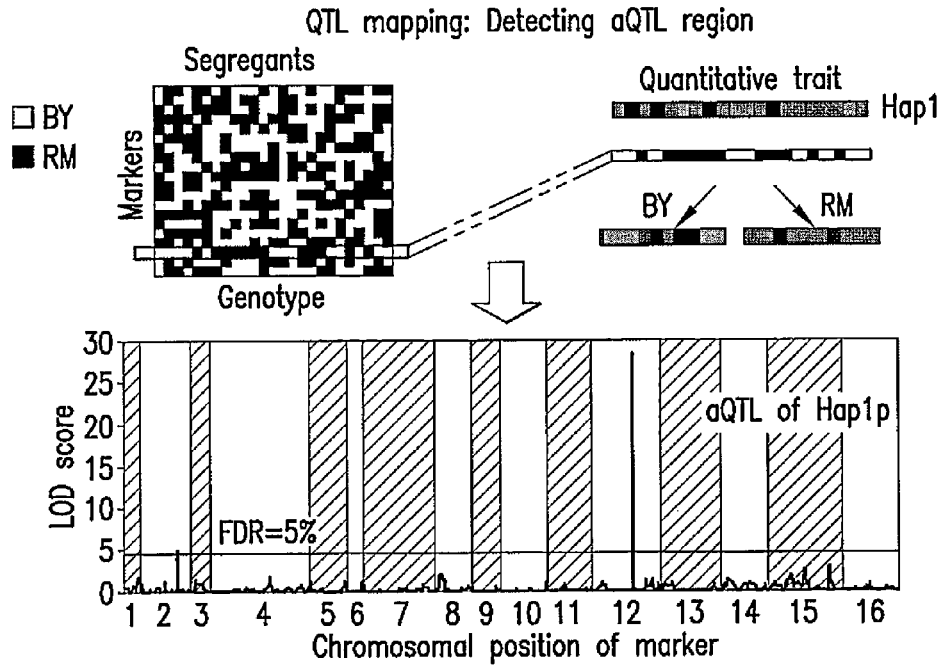

FIG. 1 illustrates an exemplary embodiment of the disclosed subject matter. In FIG. 1a, the process takes as an input a genomic upstream sequence and a position-specific affinity matrix (PSAM). These are used to generate a promoter affinity profile, as shown in FIG. 1b. The promoter affinity profile is used along with an mRNA gene expression data set to generate an inferred transcription factor activity profile. Finally, as shown in FIG. 1c, using genetic linkage analysis, an activity quantitative trait locus (aQTL) for a transcription factor (TF) is found based on the genotype data set and the inferred transcription factor activity profile. More generally, at least one genomic sequence and at least one position-specific affinity matrix can be used to generate the promoter affinity profile.

Unless otherwise defined, all technical and scientific terms used herein have the same meanings as commonly understood by one of ordinary skill in the art to which the disclosed subject matter belongs. Although methods and materials similar or equivalent to those described herein can be used in its practice, suitable methods and materials are described below.

It is to be noted that the term "a" entity or "an" entity refers to one or more of that entity. As such, the terms "a", "an", "one or more", and "at least one" can be used interchangeably herein. The terms "comprising," "including," and "having" can also be used interchangeably. In addition, the terms "amount" and "level" are also interchangeable and can be used to describe a concentration or a specific quantity. Furthermore, the term "selected from the group consisting of" refers to one or more members of the group in the list that follows, including mixtures (i.e. combinations) of two or more members.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to +/−20%, preferably up to +/−10%, more preferably up to +/−5%, and more preferably still up to +/−1% of a given value. Alternatively, particularly with respect to biological systems or processes, the term can mean within an order of magnitude, preferably within 5-fold, and more preferably within 2-fold, of a value.

Genomic Sequence

A genomic sequence refers to a nucleotide sequence of a cis-regulatory region associated with a gene. The genomic sequence controls the transcription rate or half-life of an mRNA transcript. The term "upstream genomic sequence," as used herein, generally refers to a genomic sequence which is located upstream of an open reading frame in a gene. An upstream genomic sequence generally regulates transcription. For example, the transcription rates of yeast are known to be controlled upstream, so the genomic sequence according to the presently disclosed subject matter can be an upstream genomic sequence, such as 600 bp upstream of each open reading frame. In other embodiments, however, the genomic sequence can include downstream regions, or a combination of both upstream and downstream regions of the gene sequence. Moreover, in some embodiments the genomic sequence can be a nucleotide sequence of a more distal trans-regulatory region, known as enhancers or cis-regulatory modules. Finally, the base sequence of a messenger RNA, in particular the 3' untranslated region (3'-UTR), is known to control its turnover rate, and thereby its steady state mRNA expression level.

The genomic sequences can be obtained from a database including but not limited to the Saccharomyces Genome Database, the Broad Institute database, Ensembl, the U.S. Department of Energy Joint Genome Institute (JGI), The Institute for Genomic Research (TIGR), and the National Center for Biotechnology Information databases. The genomic sequences can also be generated using methods known in the art, including but not limited to direct genome sequencing and computational or experimental annotation of gene structure.

Position-Specific Affinity Matrix (PSAM)

A position-specific affinity matrix (PSAM) includes sequence specific affinity parameters. More specifically, the data in a PSAM represents the change in binding affinity when a specific allele position within a reference gene sequence is mutated. The matrix contains the relative equilibrium constants of the transcription factor-DNA interaction, with the highest affinity nucleotide at each position scaled to a value of one.

A PSAM can be derived from a position weight matrix (PWM). A PWM is a weight matrix used to predict the strength with which the transcription factor binds to the target or cis-regulatory region. More specifically, a PWM summarizes how many sequences have a given nucleotide at a given position in the transcription factor binding site. PWMs can be obtained from an outside source such as the TRANSFAC, JASPAR, or UniProbe databases. Alternatively, PWMs can be obtained using any method known in the art, including but not limited to the GibbsSampler, AlignACE, and MEME algorithms. The PWM is used to calculate the PSAM by assuming base frequencies to be proportional to relative binding frequencies at each position within the binding site.

The PSAM can also be obtained using any method known in the art. For example, the PSAM can be obtained directly by applying the MatrixREDUCE software to genome-wide mRNA expression data, to transcription factor occupancy data, or to in vitro protein interaction data. MatrixREDUCE is described in U.S. patent application Ser. No. 11/803,777, filed May 16, 2007, the disclosure of which is incorporated herein by reference in its entirety. Genome-wide mRNA expression data can be obtained using any method known in the art, including but not limited to using DNA microarrays or RNA-seq technology. Likewise, transcription factor occupancy data can be obtained using any method known in the art, including but not limited to ChIP chip or ChIP-seq technology. In vitro protein data can also be obtained using any method known in the art, including but not limited to Protein Binding Microarray (PBM) technology.

Promoter Affinity Profile

The promoter affinity profile quantifies the affinity profile of each transcription factor for the cis- or trans-regulatory sequence of each gene. The promoter affinity profile can be used as a predictor for variation in mRNA expression. Thus, the promoter affinity profile can be used to infer transcription factor activity, because the transcription factor requires physical interaction with the cis-regulatory DNA sequence to influence transcription.

The promoter affinity profile can be determined based on the PSAM and the genomic sequence using regression analysis. The promoter affinity of a transcription factor $\phi$ on the cis-regulatory sequence $U_g$ of the gene g is denoted as $N_\phi(U_g)$.

For a given transcription factor $\phi$ and gene g, the promoter affinity is calculated as:

$$N_\varphi(U_g) = \sum_{i=0}^{L_g-L_\varphi} \sum_{j=0}^{L_\varphi-1} w_{\varphi j b(i+j,g)} \quad (1)$$

where $w_{\phi jb}$ represents the weight of the gene g for each position j and each nucleotide b of a PSAM for transcription factor $\phi$. The genomic sequence of each gene g can be used as the cis-regulatory sequence. The analysis can be performed using a software package such as MatrixREDUCE, as described in U.S. patent application Ser. No. 11/803,777, filed May 16, 2007. Promoter affinity can also be computed using methods and/or tools known in the art, including but not limited to the GOMER software. Furthermore, PWM-based promoter scores computed using CONSITE, MATCH, PATSER, rVista, or related tools, and the number of occurrences of particular oligonucleotide motifs or IUPAC consensus patterns, can also be used as a surrogate for promoter affinity.

Using this method, a promoter affinity matrix is built by calculating the promoter affinity for each combination of transcription factor $\phi$ and gene g in the promoter affinity profile. The elements of those matrices can be computed using the cis-regulatory sequences of a single reference strain only. The elements can also be computed as an average across all parental strains if their complete genome sequences are known.

Gene Expression Data Set

The gene expression data set refers to information about the mRNA expression for each combination of segregant and gene. This information is used to build a matrix containing continuous values, where rows correspond to genes and where columns contain a genome-wide mRNA expression profile of a particular segregant. The gene expression data is expressed with respect to a reference sequence. The reference sequence can be one of the parental strains. Alternatively, the reference sequence can be one of the segregants between the parental strains. The reference can also be a pooled sample of parental strains. A segregant is formed by the genetic cross of two parental strains, and differs from each parent as a result of segregation.

The gene expression data set can be obtained from a third party. For example, expression data for two parental strains and the segregants between them can be obtained from the study performed by Brem and Kruglyak (Brem, R. B. & Kruglyak, L. *Proc Natl Acad Sci USA* 102, 1572-7 (2005)) or similar studies. Expression data can also be obtained from databases such as the Gene Expression Omnibus database maintained by the National Institute of Health and the ArrayExpress database maintained by the European Bioinformatics Institute. Alternatively, gene expression data can be obtained using methods known in the art.

Inferred Transcription Factor Activity

Inferred transcription factor activity refers to data that quantifies transcription factor activity across a panel of segregants from a genetic cross, which is inferred from information about the transcription factors and the segregants.

Specifically, the transcription activity can be inferred from the gene expression data set and the promoter affinity profile because when the binding specificity is known, quantitative changes can be inferred by performing genome-wide linear regression of differential mRNA expression on the predicted in vitro binding affinity of cis-regulatory regions. The transcription factor activity is inferred in this way by performing univariate or multivariate linear regression of the genome-wide mRNA expression log-ratios on the total promoter for each transcription factor. Alternatively, non-parametric measures of segregant-specific statistical association between affinity and expression could be used as a measure of transcription factor activity. The non-parametric measures could be computed using any method known in the art, including but not limited to a spearman rank correlation, Kendall's tau, or an information theoretic measure such as the Kullback-Leibler divergence or relative entropy.

The inferred transcription factor activity for a transcription factor $\phi$ and a segregant s can be calculated using the equation:

$$E_{gs} = \beta_{0s} + \sum_{\varphi \in M} \beta_{\varphi s} N_\varphi(U_g) + \varepsilon_{gs} \quad (2)$$

where $E_{gs}$ is the logarithm base two of the ratio of the expression level of gene g in segregant s and the expression level of the same gene in a reference sample. The reference sample could be one of the parental strains, a pool of the parental strains, a pool of the segregants, or any other sample. $\beta_{\phi s}$ is a regression coefficient quantifying the activity of the transcription factor for the specific segregant and $\varepsilon_{gs}$ is a residual. A matrix defining the inferred transcription factor activity for each combination of transcription factor and segregant is built based on this equation.

Multiple linear regression with many independent variables can be affected by multicollinearity and overfitting which can result in a less precise estimate of transcription factor activity. To address this use, various variable reduction procedures known in the art can be used, including but not limited to backward regression, forward regression, and forward stepwise regression. These procedures can be used with a criterion for adding and deleting independent variables based on its coefficient of partial correlation, or F statistic. Penalized regression techniques, such as LASSO, Ridge-Regression, or Elastic Net, can also be used.

Genotype Data Set

The genotype data set refers to information regarding the parent from which a particular allele in a particular segregant is inherited. This information is used to build a matrix containing binary values whose rows correspond to genetic markers and whose columns specify from which parent each marker was inherited in a particular segregant.

The genotype data set can be obtained from a third source. For example, Brem & Kruglyak (2005) genotyped 2,957 markers for each segregant whose expression levels were determined The genotype data set can also be obtained from publicly-available databases such as the NCBI Variation database (dbSNP) and the Japanese SNP database (jSNP). Alternatively, the genotyped data set can be determined using methods known in the art, including but not limited to genotyping microarrays and high-throughput re-sequencing.

Genetic Linkage Analysis

Genetic linkage analysis is used to determine a genetic determinant that modulates transcription factor activity. More specifically, genetic linkage analysis is performed using the inferred transcription factor activity and the genotype data set to identify activity quantitative trait locus regions, which contain the particular mechanism that modulates transcription factor activity. When no data from an experimental cross is available and a population of unrelated individuals (e.g., humans) is analyzed, association analysis methods can be used instead of linkage analysis methods, in order to account for the genetic structure of the population. As used herein, the term "genetic analysis" refers to both genetic linkage analysis and association analysis.

The genetic linkage analysis can be performed using a parametric t-test, a non-parametric Wilcoxon-Mann-Whitney test, composite interval mapping, linear regression, analysis of variance, or any other methods known in the art. Some of these methods apply to haploid strains or lines, others apply to diploid strains or lines, and some apply to both. In the linkage analysis, the trait can be taken to the t-value $t_{\phi s}$ corresponding to the inferred transcription factor activity for a specific transcription factor and segregant.

For example, the segregants can be split for each specific marker and the difference between the two distributions of ridge regression coefficients can be tested using Welch's t-test and the Wilcoxon-Mann-Whitney test, Composite interval mapping (CIM) can also be used. CIM can be implemented in a software package such as in the commercially available software R/qtl. Other applicable software packages include but are not limited to PseudoMarker, CTL Cartographer, Multimapper, QTL Express, or any other QTL mapping software known in the art.

Statistical significance of regions identified by the QTL mapping process can be determined in any manner known in the art. For example, statistical significance can be determined by performing random permutation of expression log-ratios (segregants only) for each gene. Then, a false discovery rate corresponding to a given log-odds (LOD) score threshold can be computed as the ratio of the number of linkages above the threshold averaged over a number of randomized data sets.

The number of genes in an identified activity quantitative trait loci region can vary, but will generally be controlled by the density of markers and the recombination rate, which is determined in part by how many segregants are used. Therefore, increasing the number of segregants can potentially decrease the number of genes in an aQTL region.

Putative Causal Genes

As mentioned, the process above identifies an aQTL region that modulates the transcription factor activity. However, the specific gene which modulates transcription factor activity is not identified.

If the aQTL region contains the gene which encodes the transcription factor protein, that gene can be identified as the causal gene. If the aQTL region does not contain the gene which encodes the transcription factor, in one embodiment, protein-protein interaction data can be used to determine the causal gene. The protein-protein interaction data can include, e.g., physical and genetic interactions, which can be found, for example, in the BioGRID database, pairs of chromatin modifiers which influence specific transcription factors and the associated transcription factor, and kinase-substrate interaction data. If one of the genes in the aQTL region codes for a protein which interacts with the transcription factor protein, that gene can be identified as the causal gene with reasonable statistical confidence.

The causal gene can also be found in some cases by further experimentation. Specifically, for most model organisms, the use of fine mapping techniques based on additional genetic crosses can identify the causal gene and even the causal nucleotide.

EXAMPLES

The disclosed subject matter will be better understood with reference to the following Example, which is provided as exemplary of the disclosed subject matter, and not by way of limitation.

Example 1

Identifying the Genetic Determinants of Transcription Factor Activity

In the present example, data for yeast strains is used to calculate inferred transcription factor activity. The inferred transcription factor activity is then used to identify aQTL regions associated with selected transcription factors.

Methods

Genome-wide mRNA expression data from a study performed by Brem and Kruglyak (2005), which used two-color cDNA arrays, was analyzed. 496 Open Reading Frames (ORF) were excluded as rejected by Kellis et al. (Kellis, M., Patterson, N., Endrizzi, M., Birren, B. & Lander, E. S. Nature 423, 241-54 (2003). The data (GEO accession number GSE1990) covers a genetic cross between two haploid yeast strains—a laboratory strain (BY4716) and a natural isolate (RM11-1a). The dataset covers 6 biological replicates of the BY parental strain, 12 replicates of the RM parental strain, and one replicate for each of 112 haploid segregants. The study used a reference design in which all hybridizations were performed using the same BY material as a reference. $Log_2$-ratios, averaged over the dye swap, were used for all further analysis. In addition, log-ratios for 13 ORFs that were spotted twice were averaged. Each array was normalized by subtracting the mean log-ratio across all genes. For each of the segregants whose expression levels were determined, 2,957 markers were genotyped by Brem & Kruglyak (2005).

The RM11-1a sequence data is available from the Broad Institute, and as GenBank Accession No. AAEG01000000 and GI:61385875. The BY4716 sequence data is available from the Saccharomyces Genome Database (SGD; NCBI RefSeq ID NM_001133-NM_001148 and NM_001224).

A collection of 124 position weight matrices (PWMs) was obtained from a study by MacIsaac et al. (MacIsaac, K. D. et al. *BMC Bioinformatics* 7, 113 (2006)). Hap3, which has the exact same PWM as Hap5, was excluded. The convert2psam utility from the REDUCE Suite v2.0 software package was used to convert each PWM to a position-specific affinity matrix (PSAM): Pseudo-counts equal to one were added to the PWM at each position, and then base counts were divided by that of the most frequent base at each position to get an estimate for the relative affinity associated with each point mutation away from the optimal binding sequence. For each TF, the corresponding PSAM was used to predict the relative binding affinity profile across each promoter region.

Using the 123 unique PSAM, genome-wide promoter affinity was examined. Promoter affinity of the transcription factor $\phi$ on the cis-regulatory sequence $U_g$ of the gene g is denoted as $N_\phi(U_g)$. For a given $\phi$ and $U_g$, the $N_\phi(U_g)$ can be computed from PSAM as follows (Foat, B. C., Morozov, A. V. et al. *Bioinformatics* 22(14), e141-9 (2006)):

$$N_\varphi(U_g) = \sum_{i=0}^{L_g - L\varphi} \sum_{j=0}^{L_\varphi - 1} w_{\varphi j b(i+j,g)} \qquad (3)$$

where w$\phi$jb represents the weight of the gene g for each position j and each nucleotide b of a PSAM. The upstream region of length 600 bp of each gene was used as the cis-regulatory sequence and was obtained from the Saccharomyces Genome Database (Issel-Tarver, L., Christie, K. R. et al. *Methods Enzymol* 350, 329-46 (2002)). In particular, the analysis was performed using the REDUCE Suite v2.0 package.

Figure 2A:
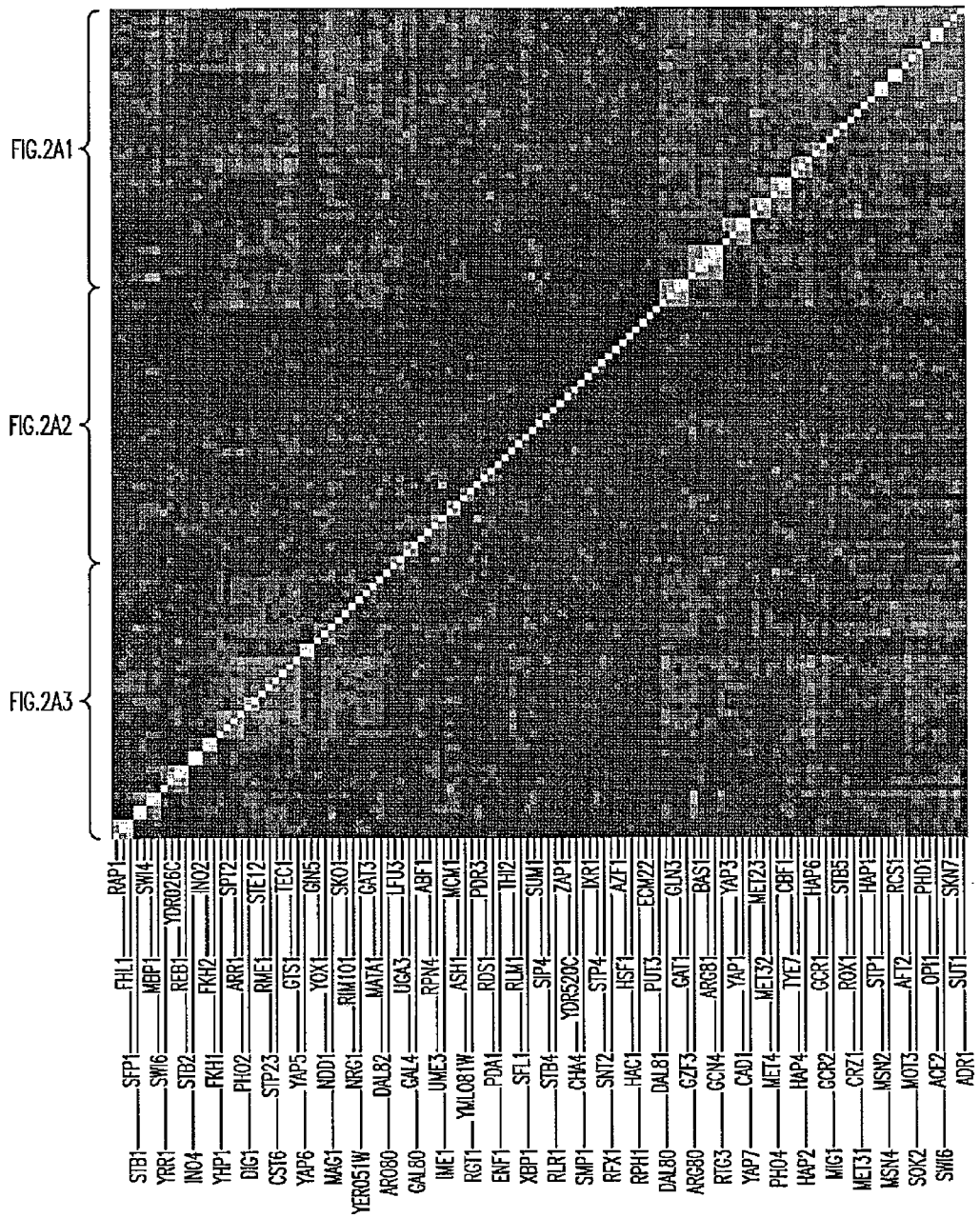
FIGS. 2A and 2B illustrate the limited correlation for pairs of transcription factor binding activity.
Figure 2B:
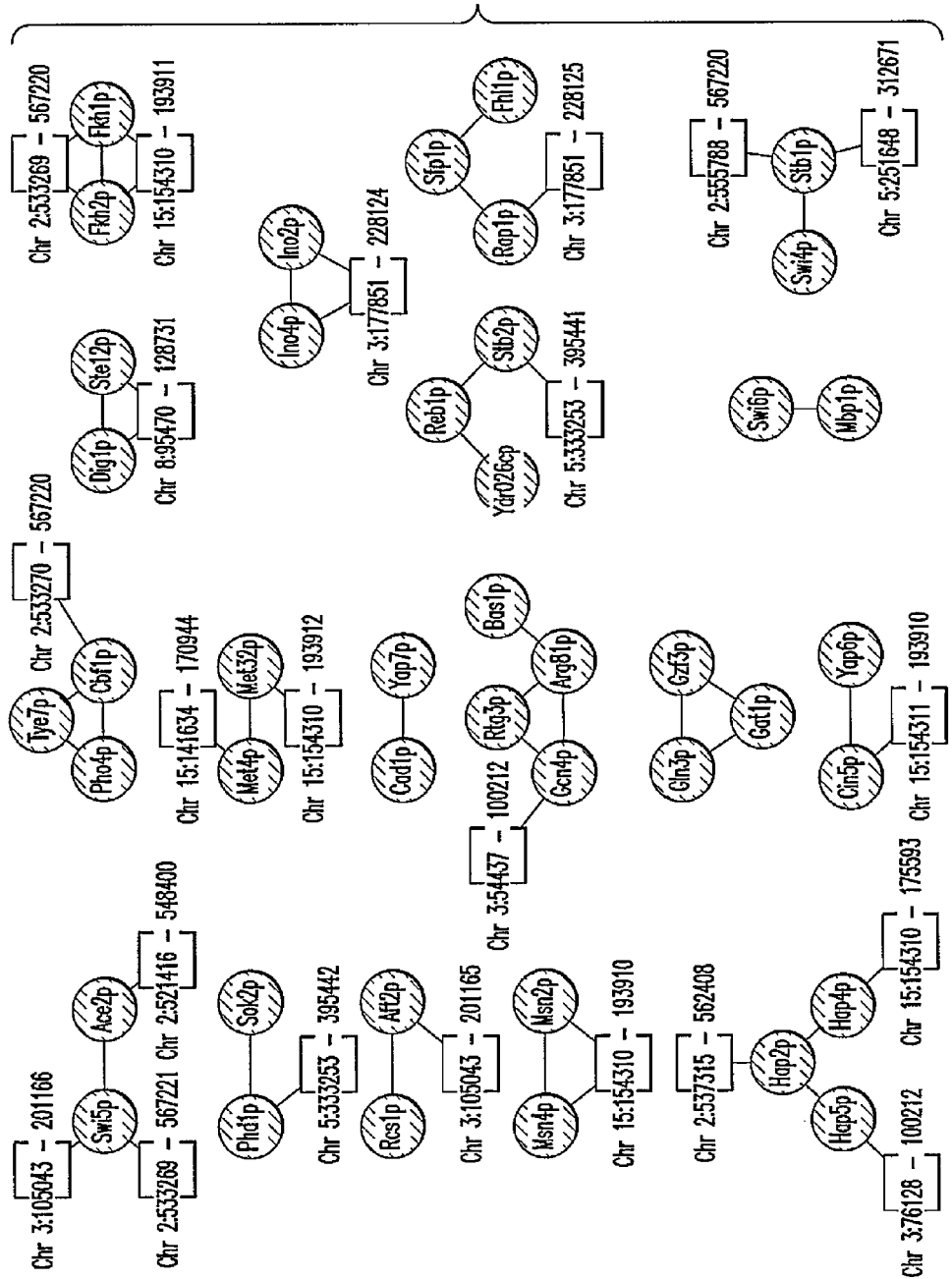

With only a few exceptions, the promoter affinity profiles were not correlated between transcription factors (FIG. 2A; the pairs of transcription factors whose promoter affinity profiles are correlated across genes, and their aQTL regions, are shown in FIG. 2B). The "total promoter affinity" was used as a predictor for variation in mRNA expression, under the assumption that in the absence of saturation and competition with other factors the occupancy of the promoter region by the transcription factor is proportional to the summed affinity profile (Bussemaker, H. J., Foat, B. C. & Ward L. D. *Annu Rev Biophys Biomol Struct* 36, 329-47 (2007)). For each segregant, multiple linear regression of the genome-wide mRNA expression log-ratios on the total promoter affinity for each TF was performed. The regression coefficients were interpreted as segregant-specific TF activities.

More specifically, the following method was used to infer transcription factor activity. The expression level of gene g in segregant s, taken as a log-ratio relative to the expression level of the same gene in the BY strain, is denoted as $E_{gs}$. For a given g and s, the inferred transcription activity can be determined by a linear model as:

$$E_{gs} = \beta_{0s} + \sum_{\varphi \in M} \beta_{\varphi s} N_\varphi(U_g) + \varepsilon_{gs} \qquad (4)$$

where $\phi$ is a transcription factor and $\beta_{\phi s}$ is a regression coefficient quantifying the activity of the transcription factor for the specific segregant s.

However, multiple linear regression with many independent variables such as all PSAMs could be affected by multicollinearity and overfitting, which can result in a less precise estimate of transcription factor activity (Neter, J., Wasserman, W. et al. *Applied linear statistical models: regression, analysis of variance, and experimental designs* (1990)). In particular, some pairs of PSAMs (such as Msn2 and Msn4, Ino2 and Ino4) are highly correlated, so multicollinearity might affect the estimation of transcription factor activity. To avoid any problems resulting from such multicollinearity, ridge regression, which minimizes the residual sum of squares subject to a penalty proportional to the $L_2$-norm of the coefficients, and gives a biased but more precise estimator of coefficients than ordinary least squares (Hoerl, A. E. & Kennard, R. W. *Technometrics* 12, 55-67 (1970)), was used.

The sequence differences in the promoter region between BY and RM strains could have an effect on the binding affinity of a specific transcription factor. Differences in binding affinity for all transcription factors were investigated as follows. First, strain-specific promoter affinities were computed using the strain-specific cis-regulatory sequence of the gene g for all 123 PSAM. Then, for a given TF, the binding occupancy differences between cis-regulatory sequences of RM and BY strains were defined as:

$$\Delta N_\phi(U_g) = N_\phi(U_g^{BY}) - N_\phi(U_g^{RM}) \qquad (5)$$

Using $\Delta N_\phi(U_g)$, the PSAMs were ranked in order of large absolute value of $\Delta N_\phi(U_g)$. Then, it was determined whether the specific PSAM shows differences between cis-regulatory sequences of RM and BY strains if $\Delta N_\phi(U_g) > N_{min}$, where $N_{min}$ is a threshold affinity, for which we used the value $N_{min} = 0.1$. By this procedure, each PSAM was tested to determine whether the PSAM shows different binding affinities to the specific point mutations or deletions using short (100 bp~300 bp) cis-regulatory sequences including the mutation.

To confirm the statistical significance of the results, the heritability of the activity of each TF was calculated as:

$$h^2 = (\sigma_s^2 - \sigma_p^2)/\sigma_s^2 \qquad (6)$$

Here $\sigma_S^2$ and $\sigma_P^2$ are the variance of the linear regression coefficient from the ridge regression across the segregants, and the pooled variance of the parental strains, respectively. To determine the statistical significance of the heritability, ridge regression was performed after independent random permutation of expression log-ratios (parents and segregants combined) for each gene (1,000 samples) and the resulting empirical null distribution was used to compute a false discovery rate (FDR).

Figure 3A:
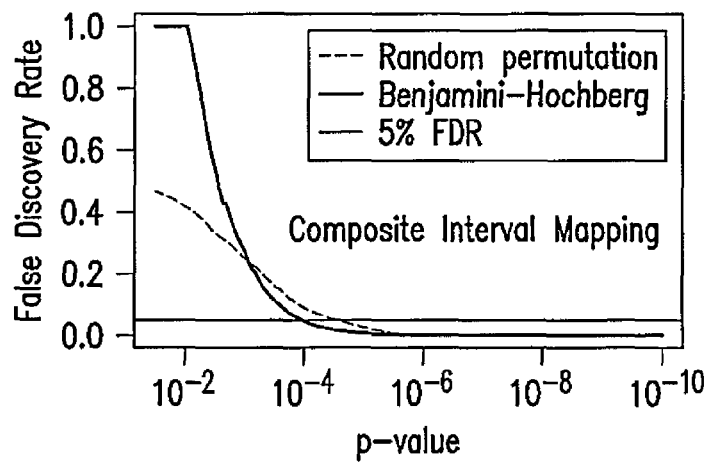
FIGS. 3A-3C illustrate estimated false discovery rate (FDR) levels from three different methods and the corresponding p-value.
Figure 3B:
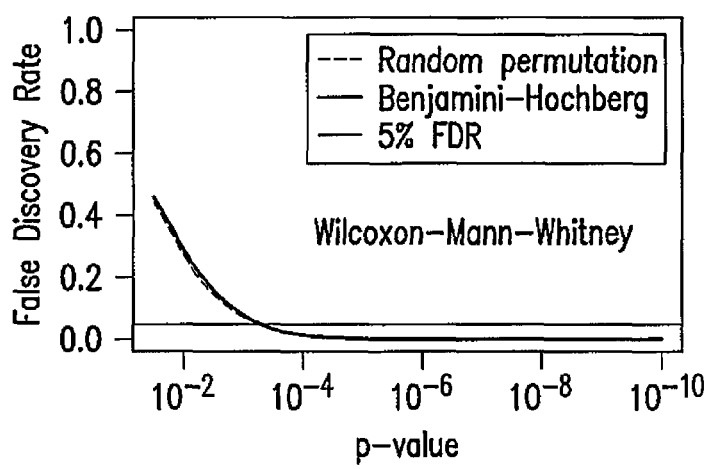
Figure 3C:
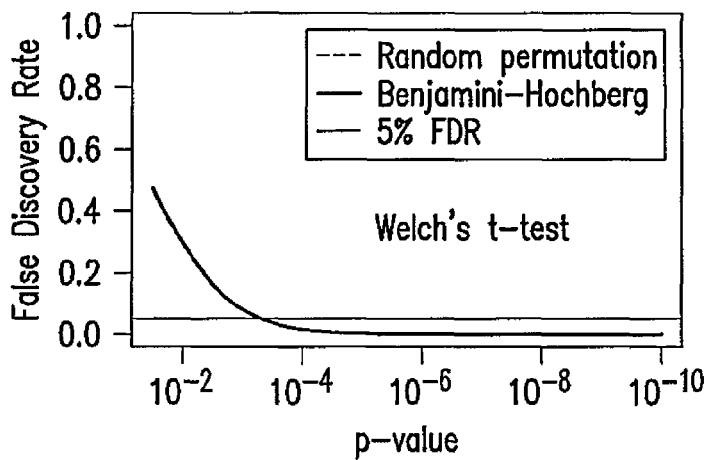

To detect significant genetic contributions to TF activity by specific loci, a split of the segregants by each specific marker was performed and a difference between the two distributions of ridge regression coefficients was calculated using Welch's t-test and the non-parametric Wilcoxon-Mann-Whitney test. Composite Interval Mapping (CIM), which uses multivariate regression on multiple markers for increased precision of QTL mapping (Zeng, Z. B. *Genetics* 136, 1457-68 (1994)), was also used, as implemented in the R/qtl package (Broman, K. W., Wu, H. Sen, S. & Churchill, G. A. *Bioinformatics* 19, 889-90 (2003)). Statistical significance was determined by performing independent random permutation of expression log-ratios (segregants only) for each gene. The FDR corresponding to a given LOD score threshold was computed as the ratio of the number of linkages above threshold averaged over 20 randomized data sets, and the number of transcripts with detected linkage. The FDR was estimated using the standard Benjamini-Hochberg procedure (Benjamini, Y. & Hochberg, Y. *Journal of the Royal Statistical Society. Series B (Methodological)* 57, 289-300 (1995)). For the CIM method, a 5% FDR based on the empirical permutation test corresponded to a LOD score>4.545 from empirical permutation tests and LOD>3.99 from step-up FDR controlling procedure. as shown in FIG. 3A (Zhu, J. et al. *Nat Genet* 40, 854-61 (2008)). For the Wilcoxon-Mann-Whitney test, the FDR=0.05 cutoff corresponded to a p-value<5.5×10$^{-4}$ from empirical permutation tests and p-value<5.0×10$^{-4}$, as shown in FIG. 3B. For the t-test, the FDR=0.05 cutoff corresponded to a p-value<4.2×10$^{-4}$ from empirical permutation tests and p-value<4.8×10$^{-4}$, as shown in FIG. 3C.

Figure 5:
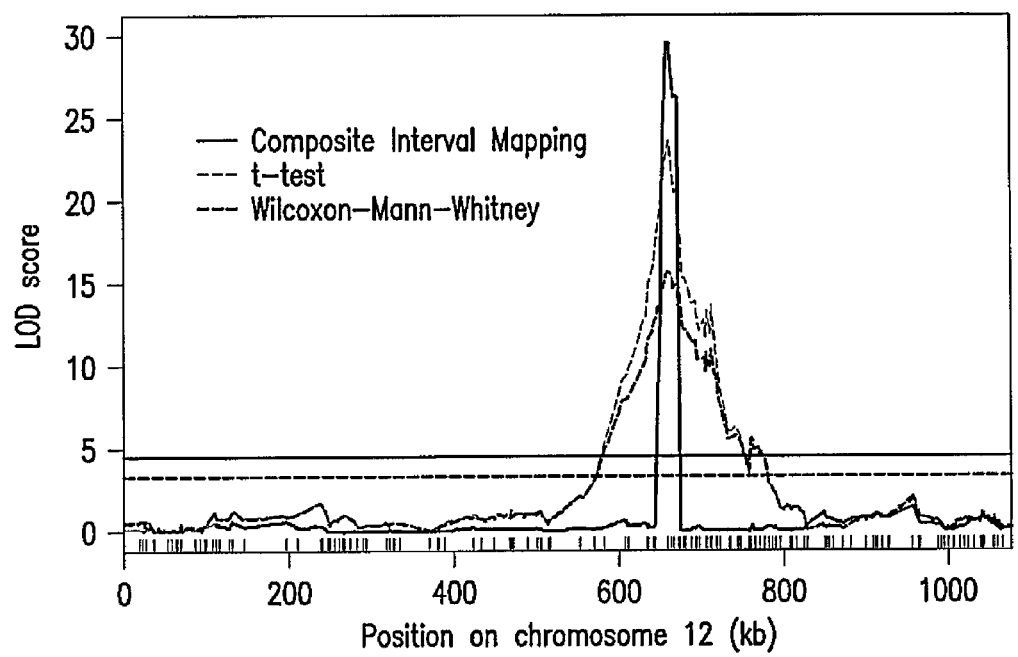
FIG. 5 compares three different methods for mapping aQTLs in terms of LOD score profiles across the HAP1 locus of chromosome XII.

A comparison of the mapping methods is illustrated in FIG. 4 for the present example. The methods used for genetic linkage analysis were Welch's t-test, the Wilcoxon-Mann-Whitney test, and composite interval mapping. FIG. 5 shows a comparison of the three different methods in terms of their LOD score profiles across the HAP1 locus on chromosome XII.

To identify putative causal genes from the aQTL regions of each specific TF, three different types of protein-protein interaction data were used: (i) physical and genetic interactions in the BioGRID database (Stark, C. et al. *Nucleic Acid Res* 34, D535-9 (2006)), (ii) interactions between chromatin modifiers and associated TFs (Steinfeld, I., Shamir, R. & Kupiec, M. *Nat Genet* 39, 303-9 (2007)), and (iii) kinase-TF interactions (Ptacek, J. et al. Nature 438, 679-84 (2005)). We computed the expected number of direct interactors among the genes in the aQTL region for a specific TF based on the total number of interactors of the TF genome-wide, the number of genes in the aQTL, and the total number of genes. Statistical significance was computed using Fisher's exact test.

Results

Figure 6:
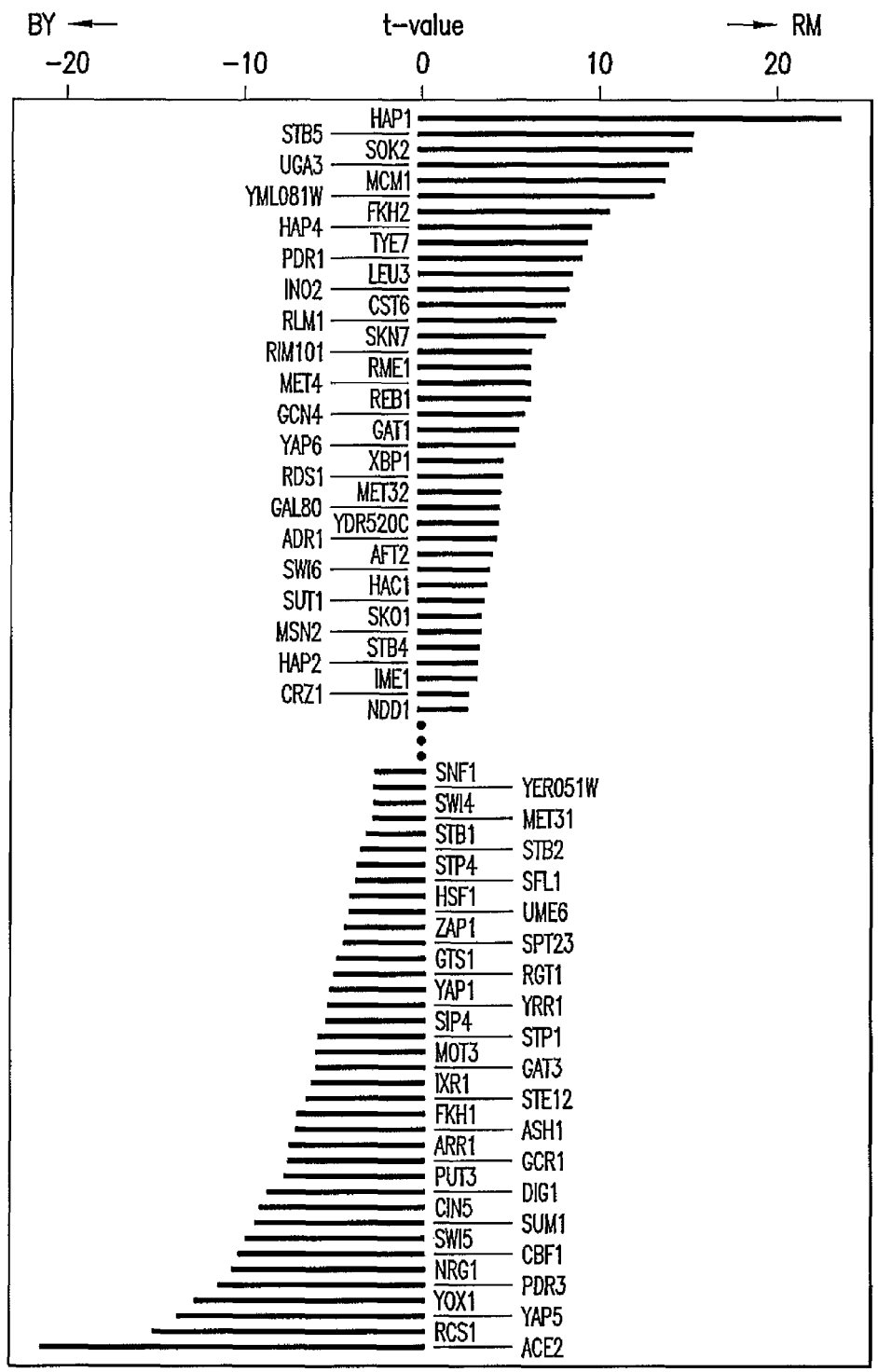
FIG. 6 illustrates differences in TF activity between the BY and RM parental strains as estimated by applying a regression procedure to the average differential mRNA expression profile between the BY and RM strains.

To establish that the TF activities inferred by the regression procedure are meaningful, their heritability was calculated. The activity of 108 of the 123 TFs tested were found to be heritable at a FDR of 5%. FIG. 6 shows the differences in TF activity between the BY and RM parental strains as estimated by applying the regression procedure to the average differential mRNA expression profile between BY and RM (Brem & Kruglyak (2005)). Shown are the t-values corresponding to the regression coefficients in the multivariate linear model that predicts genome-wide differential mRNA expression from predicted binding affinity of upstream promoter regions. Hap1p is the factor whose regulatory activity is most strongly modulated between the BY and RM strains. Indeed, it is known that a Ty1 insertion in the HAP1 coding region occurs in BY and other derivatives of the lab strain S288C (Gaisne, M., Becam, A. M., Verdiere, J. & Herbert, C. J. *Curr Genet* 36, 195-200 (1999)) and that this insertion is absent in RM (Brem, R. B., Yvert, G., Clinton, R. & Kruglyak, L. *Science* 296, 752-5 (2002)). Overall, 39 TFs are more active in RM, while 38 are more active in BY, at a 5% FDR. Merely comparing the two strains, however, does not reveal which loci are responsible for the differences in TF activity. Only genetic mapping to quantitative trait loci can provide that information.

Figure 7:
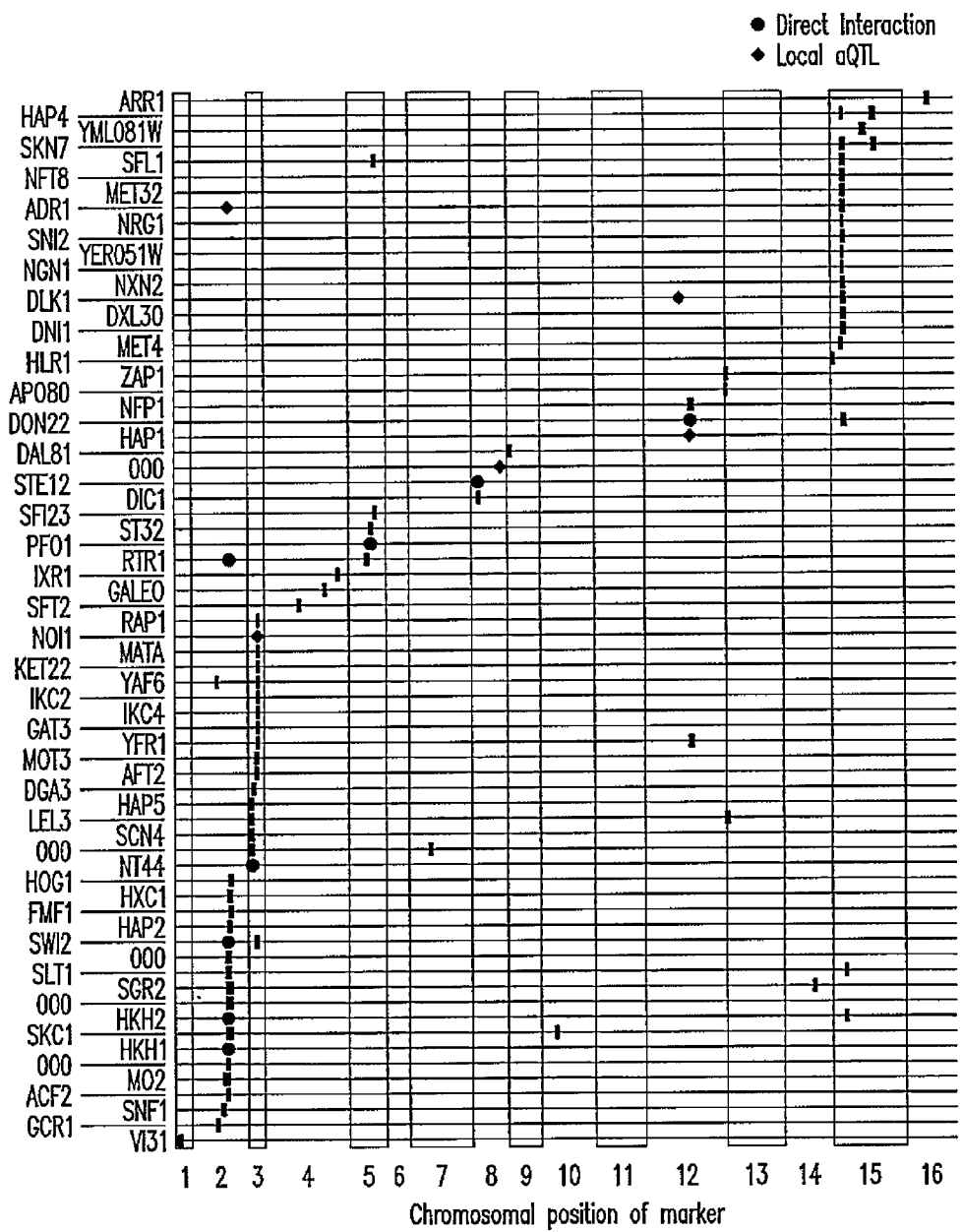
FIG. 7 provides an overview of the aQTLs identified by an exemplary embodiment of the disclosed subject matter.

FIG. 7 provides an overview of the TF-aQTL associations identified using the disclosed method. All transcription factors that have at least one significant aQTL region at a 5% FDR are shown. Transcription factors are sorted according to the chromosomal position of their maximum LOD score. A single aQTL was identified for 52 and multiple aQTLs for 17 of the 123 TFs analyzed. The results are listed in FIG. 8, and are compared to the results obtained using methods disclosed in certain prior art (Zhu et al. (2008); Lee, S. I., Pe'er, D., Dudley, A. M., Church, G. M. & Koller, D. *Proc Natl Acad Sci USA* 103, 14062-7 (2006); Ye, C., Galbraith, S. J., Liao, J. C. & Eskin, E. *PLoS Comput Biol* 5, e1000311 (2009); Sun, W., Yu, T. & Li, K. C. *Bioinformatics* 23, 2290-7 (2007)). The 15 causal genes identified are listed in FIG. 9.

Figure 10A:
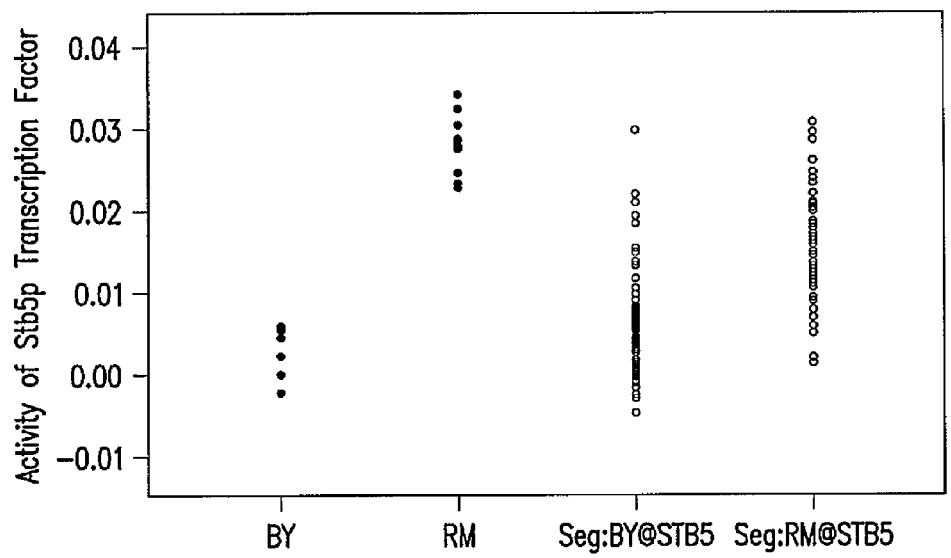
FIG. 10A illustrates the difference in Stb5p activity between the BY and RM strains.
Figure 10B:
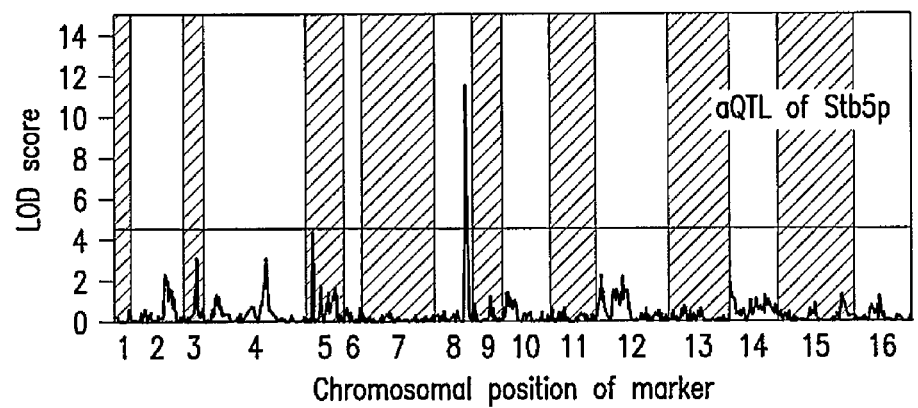
FIG. 10B shows the aQTL profile for the activity of Stb5p transcription factor.

Only three of the detected aQTL linkages are proximal. This includes the newly discovered cases of Stb5p and Rfx1p, as well as the known case of Hap1p. The probability that a locus showing aQTL linkage encompasses the gene encoding the TF itself is typically <1% (it equals the ratio of the number of genes in the aQTL and the total number of genes). Therefore, whenever such proximal linkage happens it is highly likely that the causal polymorphism resides in the coding region or regulatory region of the TF gene. Stb5p is a C2H2 zinc finger protein that serves as an activator of multi-drug resistance genes (Suthram, S., Beyer, A., Karp, R. M., Eldar, Y. & Ideker, T. *Mol Sys Biol* 4, 162 (2008)). A significant difference in Stb5p activity exists between the BY and RM strains (FIG. 10A) and this activity is highly heritable ($h^2$=82%). Highly significant proximal linkage (LOD score=11.5; Q-value=9.3×10$^{-9}$) was detected between Stb5p activity and the allelic status of the STB5 locus, as illustrated in FIG. 10B.

Figure 11:
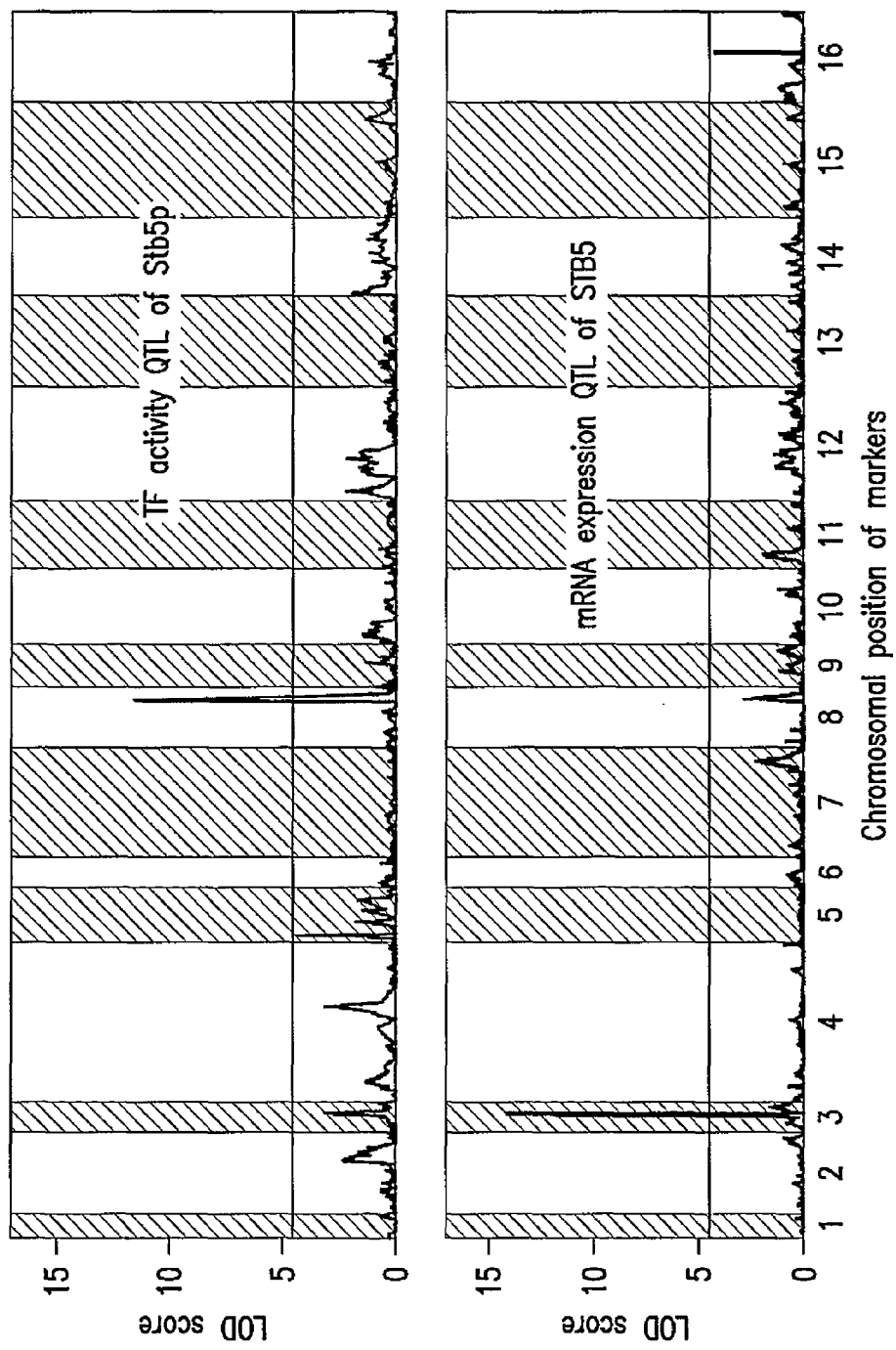
FIG. 11 compares the eQTL profile for the STB5 gene and the aQTL profile for the activity of the Stb5p transcription factor.

Alignment of the BY and RM protein sequences for Stb5p revealed five amino-acid mutations, all of which occur outside the DNA binding domain. No nucleotide differences were found in the 5' and 3' untranslated regions or <1 kb upstream of the transcription start site of STB5. Consistently, CIM analysis of the mRNA expression level of the STB5 gene did not reveal any proximal eQTL linkage, as illustrated in FIG. 11. The power of the disclosed approach is further underscored by the fact that no eQTL hotspot has been detected at the STB5 locus (Brem, Yvert et al. (2002)). The other novel proximal aQTL which was detected was for Rfx1p, a major transcriptional regulator of the DNA damage response. Consistently, the RM allele of the RFX1 gene contains a premature stop codon.

Figure 12A:
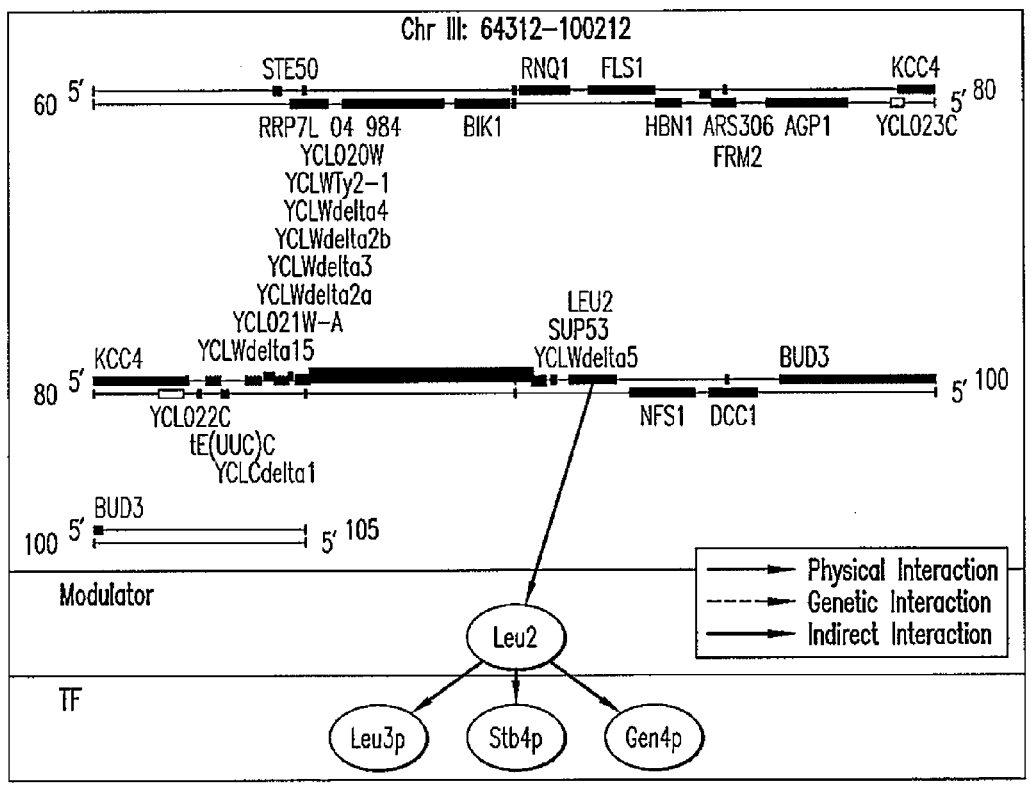
FIGS. 12A-12D illustrate causal genes identified based on protein-protein interaction data.
Figure 12B:
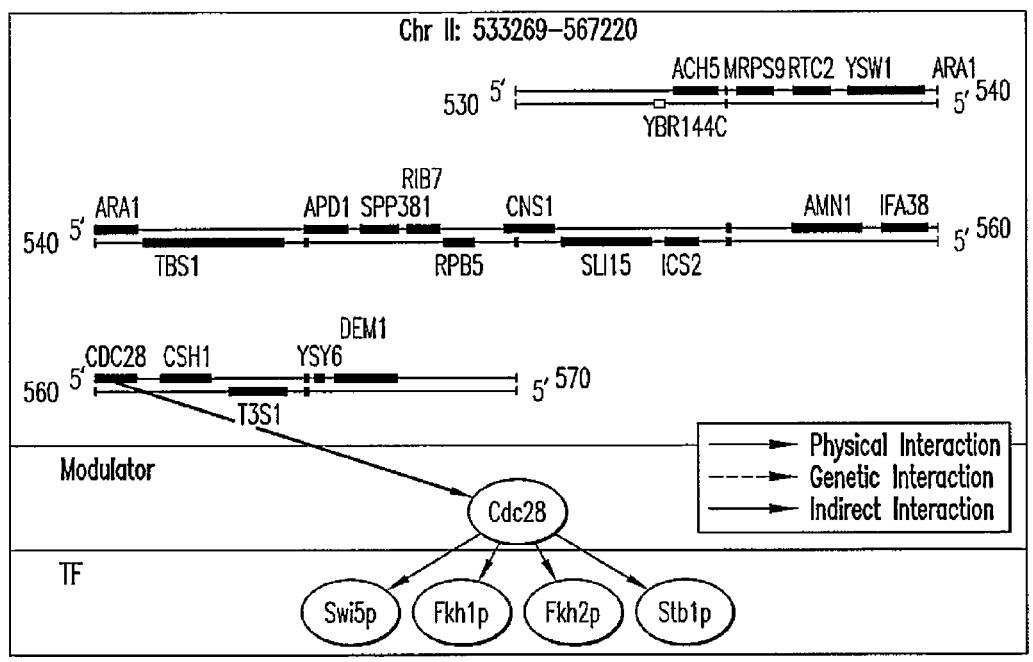

Except for the three proximal linkages described above, all linkages in FIG. 7 are distal and therefore must be due to allelic variation in genes encoding other proteins that, directly or indirectly, influence the activity of the TF. To validate the ability of the disclosed process to identify such distal aQTLs, the LEU2 locus on chromosome III was analyzed. The RM strain carries a null allele for this gene, which encodes a critical enzyme in the leucine biosynthesis pathway. Consistently, the LEU2 locus has been shown to link to a leucine auxotrophy phenotype (Brem & Kruglyak (2005)). The activities of Gcn4p, Leu3p, and Stb4p were all found to link to the LEU2 locus, as shown in FIG. 12A. Leu3p is known to specifically regulate branched amino acid biosynthesis (Friden, P. & Schimmel, P. *Mol Cell Biol* 8, 2690-7 (1988)), while Gcn4p controls the biosynthesis of a wider range of amino acids (Hinnebusch, A. G. & Fink, G. R. *Proc Natl Acad Sci USA* 80, 5374-8 (1983)). Indeed, these two factors were recently shown to be associated with an eQTL hotspot at the LEU2 locus (Ye, Galbraith et al. (2009); Sun, Yu et al. (2007)).

The identification of one or more aQTLs for a particular TF does not imply differential activity between the parental strains. Referring to FIG. 13, transgressive segregation for the activity of Ecm22p and Gcr2p was observed. In either case, the effects of two aQTLs for same TF cancel each other in both parental strains, and no differential activity between RM and BY is observed (see FIG. 6).

The genetic analysis was complemented with knowledge about physical and genetic protein-protein interactions (PPI) in order to uncover specific molecular mechanisms summarized in FIG. 7. The information provided by PPI and aQTL is highly synergistic. On the one hand, aQTL linkage can only implicate relatively large genomic regions, not individual genes, as genetic modulators of TF activity. On the other hand, while PPI data can connect a TF to a putative modulator of its activity, it would be questionable to conclude that the interaction corresponds to a functional regulatory network connection without the strict causality and directionality associated with aQTL linkage. The circles in FIG. 7 mark all instances of a direct physical or genetic interaction between a TF and one of the genes in its aQTL region(s). In all cases, the probability that a gene within the aQTL region encodes one of the direct interactors of the TF by chance is <3% (See FIG. 14). Therefore most of these genes (aQTG) are expected to encode direct or indirect modulators of the TF's activity.

Figure 12C:
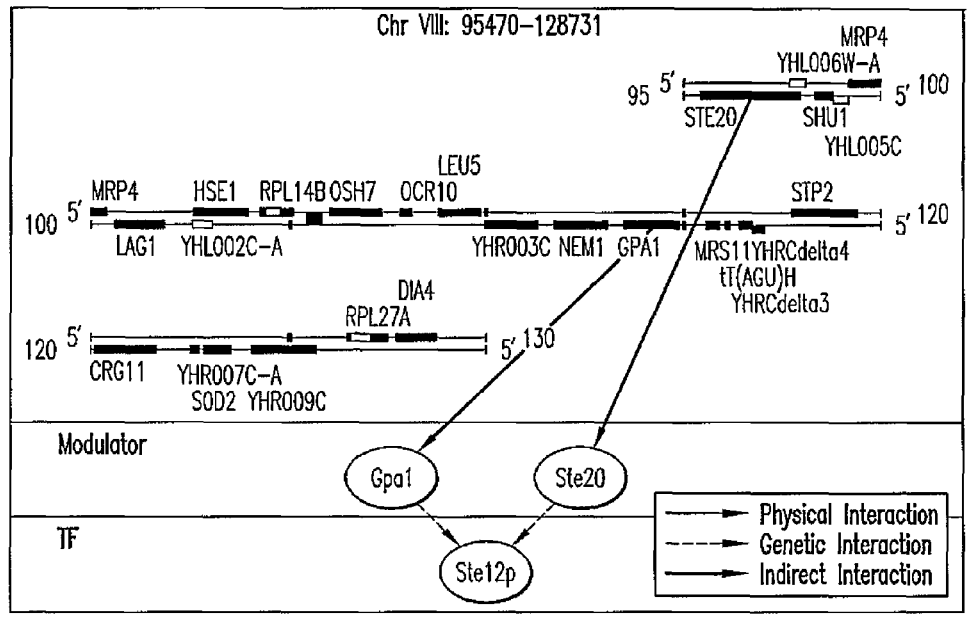

The regulatory activity of the pheromone response factor Ste12p is modulated by an aQTL on chromosome VIII containing 23 genes, shown in FIG. 12C. This locus includes the gene GPA1, which encodes the alpha subunit of a G-protein coupling to pheromone receptors (Miyajima, I. et al. *Cell* 50, 1011-9 (1987)) and is known to genetically interact with the Ste12p protein (Nakayama, N., Kaziro, Y., Arai, K. & Matsumoto, K. *Mol Cell Biol* 8, 3777-83 (1988)). A previous study (Yvert, G. et al. Nat Genet 35, 57-64 (2003)) showed that a S469I polymorphism impairs Gpa1p function in the BY strain, presumably by affecting binding to the Ste2p and Ste3p pheromone receptors. Several intermediate interactions in the pheromone response pathway (Herskowitz, I. *Cell* 80, 187-97 (1995)) influence the activity of Ste12p, which in turn explains the observed co-regulation of small gene sets enriched for transcriptional targets of Ste12p (Yvert et al. (2003)). An autoregulatory feedback loop that causes the mRNA expression level of the STE12 gene to be correlated with the regulatory activity of the Ste12p protein had previously been exploited to implicate Ste12p with this eQTL hotspot (Sun, Yu et al. (2007)).

Figure 12D:
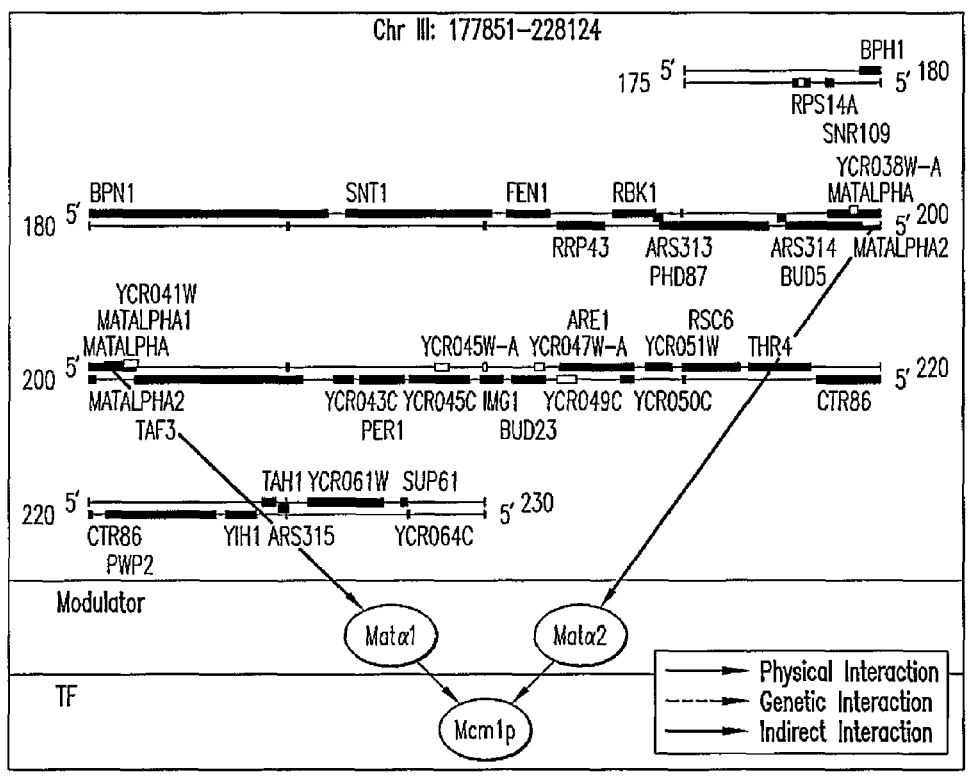

The activity of the transcription factor Mcm1p, which controls the expression of mating-type-specific genes, maps to an aQTL on chromosome III containing 32 genes. Two of these genes (MATα1 and MATα2) encode α-specific proteins known to have a direct physical interaction with Mcm1p, as illustrated in FIG. 12D. MATα2 encodes a repressor protein that acts together with Mcm1 to repress the expression of a-specific genes (Haber, J. E. *Annu Rev Genet* 32, 561-99 (1998)). This is a special case, as the haploid parental strains BY and RM are mating type α and a, respectively, and Matα1p and Matα2p are only expressed in the BY strain. The activity of Mcm1p also maps to a second aQTL: the same GPA1 locus on chromosome VIII that modulates Ste12p activity. This is biological plausible, as interaction between Mcm1p and Ste12p is known to be required to confer mating specificity to haploid yeast cells (Primig, M., Winkler, H. & Ammerer, G. *EMBO J* 10, 4209-18 (1991)).

Chromosome II was found to contain an "aQTL hotspot" whose allelic status influences the activity of no less than 10 distinct TFs. Four of these factors—Fkh1p, Fkh2p, Swi5p, and Stb1p—are associated with cell cycle control (Bahler, J. *Annu Rev Genet* 39, 69-94 (2005)). The locus contains the CDC28 gene, which encodes a cyclin-dependent kinase. Phosphorylation by Cdc28p is known to regulate the activity of Swi5p via a change in subcellular localization (Moll, T., Tebb, G., Surana, U., Robitsch, H. & Nasmyth, K. *Cell* 66, 743-58 (1991)) and that of Fkh2 by promoting interaction with a co-activator (Pic-Taylor, A., Darieva, Z., Morgan, B. A. & Sharrocks, A. D. *Mol Cell Biol* 24, 10036-46 (2004)).

Based on the aQTL mapping to the CDC28 locus in combination with high-throughput evidence of their physical interaction (Ho, Y. et al. *Nature* 415, 180-3 (2002)) with Cdc28p, it is possible that Fkh1p and Stb1p are also post-translationally modulated by Cdc28p. No direct interaction was identified for any of the other six TFs—Cbf1p, Cha4, Gcr2p, Hap2p, Sko1p, and Sut1p—whose activity maps to this aQTL hotspot. These could be indirect targets of Cdc28p, or their activity could be influenced by another polymorphism in the locus. While the locus coincides with a previously identified eQTL hotspot (Yvert et al. (2003)), CDC28 has not previously been identified as a trans-acting genetic modulator, and none of the identified TFs have been previously implicated with the hotspot.

The sign of the aQTL linkage to the CDC28 locus for Fhk2p is the opposite of that for the other three TFs identified as Cdc28p targets (FIG. 15A). For instance, while the transcriptional targets of Fkp1p are more highly expressed in segregants carrying the BY allele at the CDC28 locus, the opposite is true for the targets of Fkh2p (FIG. 15B). The same pattern holds for the inferred difference in TF activity between the two parental strains. The antagonism is particularly interesting in the case of Fkh1p and Fkh2p, and consistent with previously observed differences in function between the two factors (Hollenhorst, P. C., Pietz, G. & Fox, C. A. *Genes Dev* 15, 2445-56 (2001); Morillon, A., O'Sullivan, J., Azad, A., Proudfoot, N. & Mellor, J. *Science* 300, 492-5 (2003)). The two TFs have similar sequence specificity, and consequently their total promoter affinity profiles are correlated across genes (r=0.72). Nevertheless, the opposite influence of the CDC28 polymorphism on their activity was detected because the disclosed method uses multivariate regression, which forces TFs with correlated promoter affinity profiles to compete for the same differential mRNA expression signal. When each TF is analyzed separately using a univariate model, the CIM regression coefficients for Fkh1p and Fkh2p (incorrectly) have the same sign. This example underscores the importance of the affinity-based quantification of the matrix of regulatory connectivities between TFs and their target genes.

The foregoing merely illustrates the principles of the disclosed subject matter. Various modifications and alterations to the described embodiments will be apparent to those skilled in the art in view of the inventors' teachings herein. Features of existing methods can be seamlessly integrated into the methods of the exemplary embodiments of the disclosed subject matter or a similar method. It will thus be appreciated that those skilled in the art will be able to devise numerous methods which, although not explicitly shown or described herein, embody the principles of the disclosed subject matter and are thus within its spirit and scope.

Patents, patent applications, publications, procedures, and the like are cited throughout this application, the disclosures of which are incorporated herein by reference in their entireties.

What is claimed is:

1. A method of identifying one or more genetic determinants of transcription factor activity, comprising:
   generating, using a computer processor, an inferred transcription factor activity profile using a nucleotide sequence-specific mathematical model of gene expression regulation; and
   performing genetic analysis to identify at least one genetic determinant linked to a specific transcription factor segregant using said inferred transcription factor activity profile.

2. The method of claim 1, wherein an allelic variation in said one or more genetic determinants modulates the transcription factor activity of said specific transcription factor.

3. The method of claim 1, wherein generating an inferred transcription factor activity comprises:
   obtaining a mRNA expression data set and a promoter affinity profile; and
   generating said inferred transcription factor activity using said mRNA expression data set and said promoter affinity profile.

4. The method of claim 3, wherein obtaining a promoter affinity profile comprises:
   obtaining a position specific affinity matrix and a genomic sequence; and
   generating a promoter affinity profile using said position specific affinity matrix and said genomic sequence.

5. The method of claim 4, wherein obtaining a position specific affinity matrix comprises:
   obtaining a position weight matrix; and
   generating said position specific affinity matrix using said position weight matrix.

6. The method of claim 1, wherein said genetic determinants comprise activity quantitative trait loci.

7. The method of claim 1, wherein said genetic analysis is selected from the group consisting of genetic linkage analysis and association analysis.

8. The method of claim 7, wherein said genetic analysis comprises genetic linkage analysis.

9. The method of claim 8, wherein said activity quantitative trait loci are identified using a parametric t-test.

10. The method of claim 8, wherein said activity quantitative trait loci are identified using a non-parametric Wilcoxon-Mann-Whitney test.

11. The method of claim 8, wherein said activity quantitative trait loci are identified using composite interval mapping or another multiple locus genetic mapping algorithm.

12. The method of claim 1, further comprising connecting said specific transcription factor to one or more regulatory mechanisms using said one or more genetic determinants and protein-protein interaction data.

13. The method of claim 1, wherein said regulatory mechanism comprises a putative causal gene.

14. The method of claim 1, further comprising using a false discovery rate procedure to correct for multiple testing.

15. A method for identifying aQTL regions whose genotype modulates transcription factor activity, comprising:
   generating, using a computer processor, a promoter affinity profile using a genomic sequence and a position-specific affinity matrix;
   generating an inferred transcription factor activity profile using said promoter affinity profile and a gene expression data set; and
   identifying an aQTL region for a transcription factor using said inferred transcription factor activity profile and a genotype data set.

16. The method of claim 15, further comprising identifying a causal gene within said aQTL region using protein-protein interaction data.

17. The method of claim 15, wherein said aQTL region is identified using genetic analysis.

18. The method of claim 17, wherein said genetic analysis is selected from a group consisting of genetic linkage analysis and association analysis.

19. The method of claim 18, wherein said genetic analysis comprises genetic linkage analysis.

20. The method of claim 19, wherein said aQTL region is identified using composite interval mapping.

21. The method of claim 19, wherein said aQTL region is identified using a parametric t-test.

22. The method of claim 19, wherein said aQTL region is identified using a non-parametric Wilcoxon-Mann-Whitney test.

* * * * *

SEQUENCE LISTING

<160> NUMBER OF SEQ ID NOS: 2

<210> SEQ ID NO 1
<211> LENGTH: 29
<212> TYPE: DNA
<213> ORGANISM: Artificial sequence
<220> FEATURE:
<223> OTHER INFORMATION: Synthetic oligonucleotide

```
<400> SEQUENCE: 1
cacgataact cctcgtcgaa aactccgcc                              29

<210> SEQ ID NO 2
<211> LENGTH: 10
<212> TYPE: DNA
<213> ORGANISM: Artificial sequence
<220> FEATURE:
<223> OTHER INFORMATION: Synthetic oligonucleotide

<400> SEQUENCE: 2
cgataactcc                                                   10
```